US008578788B2

(12) United States Patent
Ito

(10) Patent No.: US 8,578,788 B2
(45) Date of Patent: *Nov. 12, 2013

(54) DEVICE AND METHOD FOR CONTINUOUSLY MEASURING HORIZONTAL FLUX OF DUSTFALL IN ATMOSPHERE

(75) Inventor: Nobuaki Ito, Tokyo (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 131 days.

This patent is subject to a terminal disclaimer.

(21) Appl. No.: 13/259,994

(22) PCT Filed: Apr. 1, 2010

(86) PCT No.: PCT/JP2010/002416
§ 371 (c)(1),
(2), (4) Date: Sep. 23, 2011

(87) PCT Pub. No.: WO2010/113520
PCT Pub. Date: Oct. 7, 2010

(65) Prior Publication Data
US 2012/0031200 A1    Feb. 9, 2012

(30) Foreign Application Priority Data

Apr. 1, 2009  (JP) .............................. P2009-089493

(51) Int. Cl.
*G01F 1/34* (2006.01)
(52) U.S. Cl.
USPC ...................................................... 73/861.42
(58) Field of Classification Search
USPC .................. 73/28.04–28.06, 170.16, 863.22, 73/863.21, 863.52, 861.42
See application file for complete search history.

(56) References Cited

U.S. PATENT DOCUMENTS 3,953,182 A * 4/1976 Roth .......................... 73/863.22
4,242,908 A   1/1981 Tombach
(Continued)

FOREIGN PATENT DOCUMENTS

JP    50-74388 U    6/1975
JP    56-31618 A    3/1981
(Continued)

OTHER PUBLICATIONS

Goossens et al., "Wind tunnel and field calibration of six aeolian dust samplers", Atmospheric Environment, vol. 34, 2000, pp. 1043-1057.

(Continued)

*Primary Examiner* — Jewel V Thompson
(74) *Attorney, Agent, or Firm* — Birch, Stewart, Kolasch & Birch, LLP

(57) ABSTRACT

A continuous atmospheric horizontal dustfall flux measurement apparatus includes: a dust sampling port that includes a ceiling plate, a side wall, and four or more partition plates; a suction pipe; a continuous dust amount measurement device that continuously measures a dust amount per unit time; a blower or a compressor; an exhaust port, wherein the side wall is a plate that has a vertical center axis and has a side surface with a substantially circular or polygonal truncated cone shape widened upward, and wherein the side wall includes a suction port which is formed at the lower end thereof so as to be connected to the suction pipe and an external air inlet which has four or more openings disposed at the same interval in the circumferential direction of the side wall at a constant height near the upper end thereof.

14 Claims, 11 Drawing Sheets

(56) References Cited

U.S. PATENT DOCUMENTS

| | | | |
|---|---|---|---|
| 4,762,009 A * | 8/1988 | Scrudto | 73/863.52 |
| 5,040,424 A | 8/1991 | Marple et al. | |
| 5,224,059 A | 6/1993 | Nitta et al. | |
| 5,412,975 A * | 5/1995 | Raabe et al. | 73/28.04 |
| 5,607,497 A * | 3/1997 | Brown | 73/864.71 |
| 2004/0038385 A1 | 2/2004 | Langlois et al. | |
| 2004/0055362 A1 | 3/2004 | Shinohara et al. | |
| 2005/0279181 A1* | 12/2005 | Trakumas et al. | 73/863.22 |
| 2012/0024084 A1* | 2/2012 | Ito | 73/863.41 |

FOREIGN PATENT DOCUMENTS

| | | |
|---|---|---|
| JP | 1-307614 A | 12/1989 |
| JP | 2-40212 A | 2/1990 |
| JP | 4-136551 U | 12/1992 |
| JP | 5-187989 A | 7/1993 |
| JP | 6-21848 B2 | 3/1994 |
| JP | 9-89727 A | 4/1997 |
| JP | 9-210942 A | 8/1997 |
| JP | 2001-50870 A | 2/2001 |
| JP | 2002-82038 A | 3/2002 |
| JP | 2002-333396 A | 11/2002 |
| JP | 2004-144664 A | 5/2004 |
| JP | 3574045 B2 | 10/2004 |
| JP | 2006-3090 A | 1/2006 |
| JP | 2006-508371 A | 3/2006 |
| JP | 2008-304277 A | 12/2008 |

OTHER PUBLICATIONS

Harrison et al. (editors), "Atmospheric Particles", IUPAC Series on Analytical and Physical Chemistry of Environmental Systems, vol. 5, 1998, pp. 46-53 (17 pages total).

Japanese Standards Association, "Low volume air sampler", JIS Japanese Industrial Standard, JIS Z 8814-1994, Edition 1, 1994, pp. 1-12 (with English translation).

International Search Report for PCT/JP2010/002416, mailed on Jun. 22, 2010.

* cited by examiner

CROSS-SECTIONAL VIEW ALONG A-A

SUCTION

CROSS-SECTIONAL VIEW

CROSS-SECTIONAL VIEW ALONG A-A

CROSS-SECTIONAL VIEW ALONG B-B

CROSS-SECTIONAL VIEW ALONG B-B

DEVICE AND METHOD FOR CONTINUOUSLY MEASURING HORIZONTAL FLUX OF DUSTFALL IN ATMOSPHERE

TECHNICAL FIELD

The present invention relates to a continuous atmospheric horizontal dustfall flux measurement apparatus and a continuous atmospheric horizontal dustfall flux measurement method.

Priority is claimed on Japanese Patent Application No. 2009-089493, filed on Apr. 1, 2009, the content of which is incorporated herein by reference.

BACKGROUND ART

In the description of the related art and the description of the invention below, the correlation between the components denoted by the same reference numerals does not indicate that the configurations and the functions thereof are the same as each other, but merely indicates, for example, a partial correlation in function or general designation. Even when the specific configurations or functions are different from each other, the same reference numerals may be given thereto.

In dust produced with various production actions and consumption actions, large dust which may freely fall in the atmosphere and has a diameter of about more than or equal to 10 μm is called dustfall. Dustfall is regarded as a significant form of environmental pollution, and there is a strong demand from society for understanding the actual conditions of the environment and preparing countermeasures. In order to understand the actual conditions of the dustfall, it is important to develop and manufacture an accurate dustfall measurement device. In particular, in the case of setting specific environmental countermeasures, it is effective to adopt a technique of searching for a place causing a problem by the combination of a specific weather condition and a dustfall amount measurement value for a short time corresponding thereto. To perform this method, there is a need to continuously measure the dustfall for a short period of one to ten minutes or less.

Among dust in an atmosphere, minute dust having a diameter of 10 μm or less and floating in the atmosphere substantially without falling freely is called a suspended particulate matter (SPM). Since the SPM substantially moves in accordance with the ambient atmospheric flow, only the concentration of the SPM in the atmosphere may be considered as a problem in the environmental influence evaluation of dust. For this reason, in the case of measuring the actual state of the SPM in the atmosphere, for example, a constant amount of atmosphere is suctioned and filtered, whereby the concentration of the dust in the atmosphere is calculated. On the other hand, the larger dustfall does not move completely in accordance with the ambient atmospheric flow. The dustfall falls in the atmosphere at a different speed in accordance with the density or the size of the particle so as to be deposited on the ground. When there is a barrier in the atmosphere, the dustfall collides with the barrier and adheres thereto. For this reason, the environmental influence of the dustfall mainly occurs due to contamination caused by the deposition or the adherence of the dustfall to a specific material. Therefore, in order to evaluate the environmental influence of the dustfall, it is not sufficient to only measure the concentration of the dustfall in the atmosphere, and there is a need to measure the amount of the dustfall passing through a unit area of an inspection plane fixed to a space per unit time, that is, the flux of the dustfall.

The flux of the dustfall, which is a subject of the environmental problem, may be divided into a vertical flux and a horizontal flux. In the vertical flux, the inspection plane is horizontal, and is mainly concerned with the evaluation of the deposition of the dustfall on the ground. In the horizontal flux, the inspection plane is vertical, and is mainly concerned with the evaluation of the adherence of the dustfall to a vertical surface such as a wall of a building. The atmospheric flow outside a building, that is, wind may be regarded as having a vector in the horizontal plane according to an average for a long period of time. For this reason, the vertical flux is not influenced by the wind speed. On the contrary, the horizontal flux is a function of the wind speed. More specifically, the flux of the dustfall may be defined by the following equation.

[vertical flux of dustfall]=[concentration of dustfall]×
 [falling speed of dustfall]

[horizontal flux of dustfall]=[concentration of dustfall]×[wind speed of component perpendicular to inspection plane]

Likewise, in order to measure the horizontal dustfall flux, there is a need to understand the wind direction or the wind speed during measurement at all times. Furthermore, the measurement device needs to have a function of collecting the flow of the dustfall in the wind direction at all times. On the other hand, in the measurement of the vertical flux of the dustfall, such consideration is not needed, and the horizontal dustfall flux may be measured in a simpler manner. For this reason, in the public management of dustfall, a device solely measuring the vertical flux, for example, a deposit gauge shown in FIG. 1 has been used. In the deposit gauge, a dust sampling port 1 is formed in a trumpet shape which is opened upward. The dustfall is collected in a manner such that the dustfall falling and deposited on the inner surface of the dust sampling port 1 is made to flow into a collection container 25 present below the dustfall sampling port 1 by rainwater or water used for collecting the collected dustfall.

Further, the horizontal dustfall flux may be formally transformed from the vertical flux in the following equation.

[horizontal flux of dustfall]=[vertical flux of dustfall]×
 [wind speed of component perpendicular to
 inspection plane]/[vertical falling speed of dustfall]

Here, the wind speed of the component perpendicular to the inspection plane is defined as below. First, a virtual inspection plane is perpendicularly installed at a point which causes a problem. At this time, the wind speed of the component perpendicular to the inspection plane is a component in accordance with the direction perpendicular to the inspection plane in the wind speed at the point.

For this reason, even when the horizontal dustfall flux is regarded as a problem, a simple evaluation using the measurement result of the vertical flux and the equation has been conducted. However, in fact, it is difficult to quantitatively measure the falling speed of the dustfall variously changing with time. For this reason, a large error occurs when calculating the horizontal flux of the dustfall on the basis of the equation. Therefore, when the horizontal flux is a problem, it is desirable to directly measure the horizontal flux from the viewpoint of measurement precision.

As a dustfall trapping device that directly measures a horizontal flux of dustfall, a device is disclosed which naturally circulates wind inside a dust sampling port 1, traps dustfall by collecting a portion of the dustfall introduced with the wind through inertial dust collection or gravitational dust collection, and measures the horizontal flux of the dustfall according to the result. Non-patent Document 1 discloses a plurality of particle trapping devices of this type.

As the representative type, a big spring number eight (BSNE) is shown in FIGS. 2A and 2B. In the BSNE, an atmosphere naturally flowing from an external air inlet 10 into the dust sampling port 1 is decelerated inside the device as the flow passage is widened. Subsequently, as depicted by a flow line of an atmospheric flow 17 passing through the dust sampling port, the atmosphere naturally flows outward from an exhaust port 8, which is a metallic mesh provided on the top surface of the device. The wind decelerates inside the dust sampling port, so that the retention time of the dustfall inside the dust sampling port 1 increases, and the dustfall falls freely by a long distance inside the dust sampling port in the meantime.

Likewise, the portion inside the dust sampling port 1, exhibiting an effect of reducing the wind speed inside the dust sampling port so as to be lower than the wind speed of the flow 15 of the external air so as to increase the retention time of the dustfall inside the dust sampling port 1 and increasing the falling distance of the dustfall, is referred to as a wind reduction area 13 in the specification.

The dustfall in the atmosphere falling in the wind reduction area 13 falls freely or collides with the wall of the downstream end of the device when passing through the inside of the device as depicted by the flow line of trapped dustfall 19. Subsequently, the trapped dustfall 19 passes through a metallic mesh 33 disposed below the flow passage and is trapped by a particle trap 32.

A portion of the dust inside the dust sampling port 1 flows into the external air from the exhaust port 8 as depicted by the flow line of dustfall 20 passing through the dust sampling port. Further, the entire device is rotatable in the horizontal direction, and the external air sampling port 10 is made to be automatically directed toward the upward wind direction at all times due to the action of a blade 23 and a rotary shaft 24 provided in the device. Even though this device really has a simple structure, the trapped dustfall is manually collected at one time. For this reason, in the BSNE, it is difficult to continuously measure the transition of the time-series dustfall trapping amount for a short period.

Further, in the BSNE, the dustfall trapping surface is long and large along the wind direction. For this reason, it is difficult to accumulate the dustfall in a narrow space area to increase the concentration of the dustfall. Further, it is difficult to further provide a device highly precisely measuring the dustfall amount, for example, the dustfall mass in the BSNE. This is because the mass of the trapped dustfall is much smaller than the mass of the BSNE body as the trapping device. For this reason, it is essential to independently measure only the mass of the dustfall after spatially separating and concentrating the dustfall from the BSNE body.

Non-patent Document 1 introduces a suspended sediment trap (SUSTRA) or a Modified Wilson & Cooke sampler (MWAC) as the collector for the horizontal dustfall flux. The collection principle of the SUSTRA is basically the same as that of the BSNE. The MWAC dust sampler shown in FIGS. 7A and 7B includes: a collection bottle with an external air inlet 10 which is an L-shaped pipe having an opening provided in the upward wind direction; and an exhaust port 8 which is an L-shaped pipe having an opening provided in the downward wind direction. The MWAC does not have a special mechanism that makes the external air inlet 10 of the dust sampling port follow the wind direction.

In order to continuously measure the horizontal flux of the dustfall, as described above, the trapped dustfall needs to be concentrated at a narrow space area to increase the density thereof, and the dustfall needs to be introduced into a certain continuous dust amount measurement device 6. In order to exhibit such an effect, the dustfall in the atmosphere needs to be introduced into the dust sampling port 1 together with the atmosphere, and air containing the dustfall inside the dust sampling port 1 is suctioned so as to be introduced into the continuous dust amount measurement device 6. During a time in which the dust is suctioned, the continuous dust amount measurement device 6 continuously measures the dustfall amount per unit time.

As described above, the dustfall does not completely move in accordance with the flow of the wind. For this reason, for example, in the dust sampling port 1 of the dustfall amount measurement device, the suction may be performed in the direction different from the wind direction as shown in FIG. 3 or the suction may be performed at a speed different from the wind speed as shown in FIG. 4. In this case, suctioning of the dustfall in the external air to the dust sampling port 1 together with suctioned atmosphere 16 is not limited thereto. As in the dustfall 18 in the external air of FIGS. 3 and 4, the ratio of the dustfall bypassing the external air inlet 10 is large to a degree which may not be ignored. Furthermore, the ratio of the bypassing dustfall is sensitively influenced by various weather conditions, characteristics of the dustfall, and the shape of the device. For this reason, it is difficult to predict the ratio of the bypassing dustfall.

Therefore, the suction type shown in FIGS. 3 and 4 is not desirable as the dustfall collection method for measuring the horizontal dustfall flux. Specifically, such a dustfall sampling method is shown in Patent Documents 1, 2, and the like. In these devices, since the external air suction speed is constant in the external air inlet 10 at all times, the wind speed of the external air is generally not equal to the external air introduction speed.

Further, the direction of disposing the external air inlet 10 is generally fixed in many cases. Therefore, the normally changing wind direction of the external air is not generally equal to the direction of the external air inlet 10. For this reason, as disclosed in Non-patent Document 4, the dust trapping efficiency of the particle having a diameter more than 10 µm in this type of dust sampling port 1 is extremely small such as to be a several % or less.

Further, since the dust trapping efficiency is strongly influenced by the ambient measurement conditions such as a wind speed, it is difficult to highly precisely understand the outdoor dust trapping efficiency. For this reason, in the dust sampling port 1 collecting the atmospheric dustfall in order to measure the horizontal dustfall flux, there is a need to introduce an atmosphere at substantially the same speed as the wind speed and the wind direction of the external air.

In a dust trapping method of introducing an atmosphere into the dust sampling port 1 at the same speed as the wind speed and the wind direction of the external air, there is a method called uniform suction. In the uniform suction, the wind speed of the external air is measured, and a suction flow rate of a separate blower is controlled so that the atmosphere introduction speed at the inlet of the dust sampling port 1 matches the wind speed. This method is mainly applied to the case of measuring the flux of the dust inside a wind tunnel of which the wind direction is fixed as shown in the example of Non-patent Document 2. Patent Documents 4 and 5 disclose a method of controlling the direction of the dust sampling port 1 so that the direction matches the wind direction at all times in accordance with the control of the wind speed at the time of applying the uniform suction to trap the dustfall outdoors for the purpose of obtaining the horizontal flux of the dustfall. Such a method is the most reliable method of trapping the dustfall concerned with the horizontal flux measurement. However, in this case, a complex configuration and a complex control are needed due to a flow rate control device or a rotation mechanism of the dust sampling port, and the device may easily become expensive and increase in size. For this reason, this can not be considered a simple measurement method.

Further, weather resistance is an important function for continuously measuring the horizontal flux of the dustfall for a long period at an outdoor place. In particular, a problem such as a failure occurs in many continuous dust amount measurement devices when raindrops intrude into a measurement unit in the case of rainfall. Therefore, there is a need to provide a structure capable of preventing raindrops from intruding into the dust sampling port 1 or removing raindrops intruding into the dust sampling port 1. In general, a manual simple dust trap such as the BSNE does not include a mechanism of preventing raindrops from intruding into the external air inlet 10 or a mechanism of removing raindrops inside the device.

As a method of preventing raindrops from intruding into the dust sampling port 1, there is known a method of providing a louver in the dust sampling port 1 or a method of Patent Document 1. In the device of Patent Document 1, the dust sampling port 1 has a structure shown in FIG. 4. In addition, an impactor is provided so as to remove dustfall or raindrop with a diameter more than 10 μm. However, as for the principle of preventing raindrops from intruding into the dust sampling port 1 of this method, the flow passage of the atmosphere flowing into the dust sampling port 1 is abruptly changed to remove raindrops which may not follow the atmospheric flow. For this reason, in this method, large dust such as dustfall is removed together with the raindrops inside the dust sampling port 1. Therefore, this method is not suitable as a method of trapping dustfall according to the object of the invention.

Next, the continuous dust amount measurement device of the related art will be described. As the continuous dust amount measurement device, various types are proposed. The simplest method is a low volume sampler shown in Non-patent Document 3. In this device, the dustfall in the suctioned atmosphere is filtered by a filter, and a variation in weight of the filter is measured off-line so as to calculate the mass of the trapped dust. In the case of this device, the filter needs to be replaced after a short period in order to perform the continuous measurement. For this reason, this method is not practical from the viewpoint of burden of work. Furthermore, a device increasing the suctioned flow rate of the low volume sampler for the measurement at a short time is called a high volume sampler. Therefore, the principle, the structure, and the reliability of the high volume sampler are substantially the same as those of the low volume sampler.

Further, Patent Document 6 discloses a continuous dust amount measurement device shown in FIG. 5. In this device, a trumpet-shaped dust sampling port 1 with an upward opening is provided, so that the dustfall may be trapped and the mass of the dust may be continuously and precisely measured using a β-line absorption type mass measurement device.

In this device, the atmosphere flowing into the dust sampling port largely and rapidly turns inside the dust sampling port, and most of the atmosphere advances along the flow passage 17 so as to flow to the outside of the system. When the wind speed of the external air increases, the amount of the dustfall flowing into the dust sampling port 1 also increases, but the turning flow speed inside the dust sampling port 1 also increases in proportion to the wind speed. As a result, the amount of the dustfall flowing to the outside of the system from the inside of the dust sampling port increases. For this reason, the dustfall trapping efficiency is hardly influenced by the wind speed of the external air, and the vertical flux of the dustfall may be suitably measured. However, this device is not suitable for the measurement of the horizontal flux of the dustfall. In the device, a failure may occur in the device when suctioning raindrops in many cases. For this reason, generally, this device includes a mechanism automatically covering the opening of the dust sampling port 1 in the case of rain, and does not perform the measurement in the case of rain.

Further, Patent Document 7 discloses a particle counter 11 which is a light scattering type particle counter. This device is operated in accordance with the principle in which each dust particle passing through a measurement unit is irradiated with a laser beam and the reflection and the intensity of the scattered light are detected so as to determine the presence of dust particles with a predetermined diameter or more. This device may measure the number of dust particles in the suctioned atmosphere. However, when a standard sample of dust is separately provided and a relationship between the number of dust particles and the mass of dust is determined in advance, the number of dust particles detected at the particle counter 11 may be converted into the mass of dust.

Further, since there is no need to trap the dust in this device, a filter need not be essentially provided. Furthermore, a device is also available which sprays sheath air corresponding to clean air to the periphery of the suctioned external air in the same axis as that of the flow of the external air. Accordingly, dust or fog dip contained in the suctioned external air may be collected inside a measurement flow passage. However, there is a problem in that a failure occurs in the device when suctioning a large amount of raindrops as in the above-described other devices.

Further, Patent Document 8 discloses a light transmission type particle concentration meter. In this device, dust suctioned together with atmosphere inside the device is irradiated with light. At this time, the light transmission amount of the light attenuated due to the effect of the reflection or absorption of the dust is measured and converted into the concentration of the dust. The weather resistance is the same as that of the particle counter 11.

RELATED DOCUMENTS

Patent Documents

[Patent Document 1] Japanese Unexamined Patent Application, First Publication No. 2006-3090
[Patent Document 2] Japanese Patent Publication No. 3574045
[Patent Document 3] Japanese Unexamined Patent Application, First Publication No. 2004-144664
[Patent Document 4] Japanese Unexamined Utility Model Application, First Publication No. H4-136551
[Patent Document 5] Japanese Unexamined Patent Application, First Publication No. H5-187989
[Patent Document 6] Japanese Examined Patent Application, Second Publication No. H6-021848
[Patent Document 7] Japanese Unexamined Patent Application, First Publication No. 2002-82038
[Patent Document 8] Japanese Unexamined Patent Application, First Publication No. H1-307614

Non-Patent Documents

[Non-patent Document 1] Goossens, D., Offer, Z. Y.: Atmospheric Environment, vol. 34 (2000), pp. 1043-1057

[Non-patent Document 2] Japanese Industrial Standards, JIS Z 7151
[Non-patent Document 3] Japanese Industrial Standards, JIS Z 8814
[Non-patent Document 4] R. M. Harrison, R. E. van Grieken: Atmospheric Particles, John Wiley & Sons (England), 1998, pp. 47-53

SUMMARY OF INVENTION

Problems to be Solved by the Invention

As described above, in the horizontal dustfall flux measurement device of the related art, there are problems in that measurement may not be continuously performed with a short cycle period, dustfall trapping efficiency may be low, an increase in size of the device may be unavoidable, the structure may be expensive and complex, and a rainfall countermeasure may not be considered.

It is an object of the invention to provide an atmospheric horizontal dustfall flux measurement device that has high dustfall trapping efficiency, has a small, simple, and cheap structure, and is capable of performing continuous measurement for a short period of one minute or so at an outdoor place. It is an object of the invention to provide a device capable of considering rainfall countermeasure.

Means for Solving the Problem

As a result of the inventor's study for dustfall measurement, the solution is contrived as follows.

(1) According to one aspect of the invention, there is provided a continuous atmospheric horizontal dustfall flux measurement apparatus including: a dust sampling port that includes a ceiling plate, a side wall, and four or more partition plates; a suction pipe; a continuous dust amount measurement device that continuously measures a dust amount per unit time; a blower or a compressor; an exhaust port, wherein a flow passage is formed by sequentially connecting the dust sampling port, the suction pipe, the continuous dust amount measurement device, the blower or the compressor, and the exhaust port so that the suctioned air flows in series, wherein the side wall is a plate that has a vertical center axis and has a side surface with a substantially circular or polygonal truncated cone shape widened upward, wherein the side wall includes a suction port which is formed at the lower end thereof so as to be connected to the suction pipe and an external air inlet which has four or more openings disposed at the same interval in the circumferential direction of the side wall at a same height near the upper end thereof, wherein the ceiling plate has a substantial disk shape, the diameter thereof is larger than the diameter of the horizontal cross-section of the upper end of the side wall, the center axis of the ceiling plate matches the center axis of the side wall, and the ceiling plate is connected to the upper end of the side wall so as to come into contact therewith, wherein four or more partition plates are four or more flat plates which are disposed in a vertical plane so as to divide a space surrounded by the side wall into fan-shaped areas with the same size in the horizontal cross-section, are connected to each other on the center axis, and have the same height, and wherein the partition plates are connected to the side wall and to the ceiling plate without any gap therebetween.

(2) In the continuous atmospheric horizontal dustfall flux measurement apparatus according to (1), the ceiling plate may include a peak portion that extends outward in relation to the upper end of the side wall, and wherein when Equation (1) is defined as ((representative wind speed of external air)/(free falling speed of dustfall desired to be trapped))×(axial length between lower surface of ceiling plate and lower end of external air inlet), the length of the peak portion along the radial direction of the ceiling plate may be smaller than the value of Equation (1).

(3) In the continuous atmospheric horizontal dustfall flux measurement apparatus according to (1) or (2), the continuous dust amount measurement device and the blower or the compressor may constitute a particle counter.

(4) In the continuous atmospheric horizontal dustfall flux measurement apparatus according to (1) or (2), the continuous atmospheric horizontal dustfall flux measurement apparatus may further include: an aerovane that measures an average wind speed of external air per unit time; a calculation device that receives the average wind speed value measured by the aerovane and the momentary dustfall amount measurement value measured by the continuous dust amount measurement device as an input value and calculates a momentary external air dustfall concentration on the basis of Equation (2) below: (momentary external air dustfall concentration)=(momentary dustfall amount measurement value)/((average wind speed measurement value)×(effective opening area of external air inlet)) . . . (2); and an output device that stores or displays the momentary external air dustfall concentration calculated by the calculation device.

(5) In the continuous atmospheric horizontal dustfall flux measurement apparatus according to (1) or (2), the length of each partition plate along the axial direction of the side wall may be twice or more the length of the external air inlet along the axial direction of the side wall.

(6) In the continuous atmospheric horizontal dustfall flux measurement apparatus according to (1) or (2), the length of each partition plate along the axial direction of the side wall may be 0.5 times the axial length of the dust sampling port.

(7) In the continuous atmospheric horizontal dustfall flux measurement apparatus according to (1) or (2), the blower or the compressor may suction a part or all of dustfall flowing into the dust sampling port along with air together with a part of the air inside the dust sampling port, introduce the dustfall and the air into the continuous dust amount measurement device through the suction pipe from the suction port, and discharge the suctioned air from the exhaust port.

(8) According to one aspect of the invention, there is provided a continuous atmospheric horizontal dustfall flux measurement method using the continuous atmospheric horizontal dustfall flux measurement apparatus according to (1) or (2), a value obtained by dividing the amount of the dustfall trapped per unit time by the effective opening area of the external air inlet may be calculated as the horizontal flux of the dustfall.

Advantageous Effects of Invention

According to the invention, it is possible to continuously measure a horizontal flux of dustfall with high precision for a short period of one minute or so using a simple structure. Further, in addition to this, in one aspect of the invention, it is possible to realize an all-weather continuous atmospheric horizontal dustfall flux measurement device capable of performing measurement without any failure in the case of rain.

DESCRIPTION OF EMBODIMENTS

Figure 1:
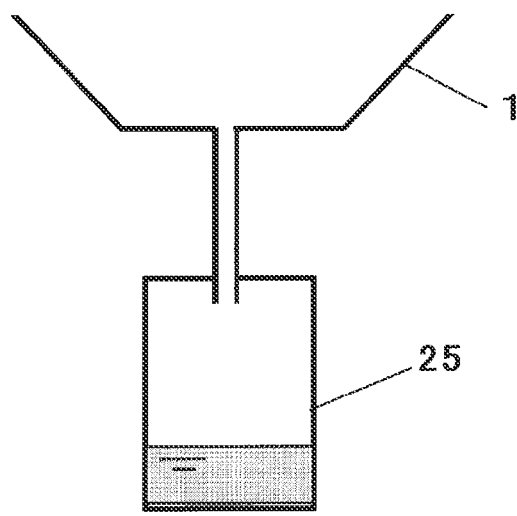
FIG. 1 is a schematic diagram of the related art.
Figure 2A:
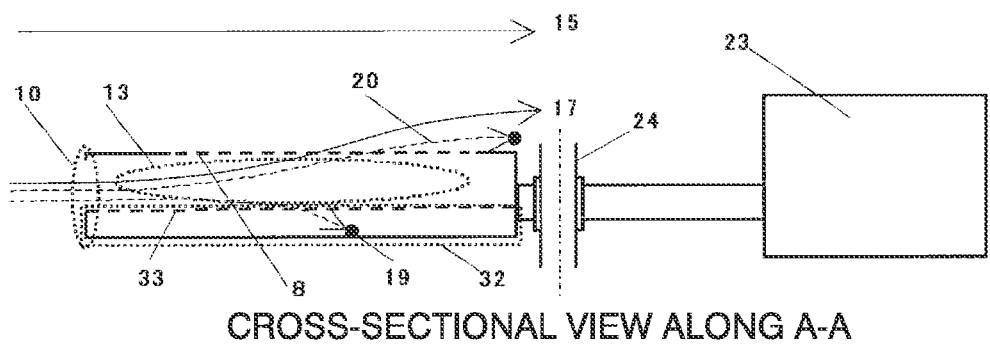
FIG. 2A is a schematic cross-sectional view of the related art.
Figure 2B:
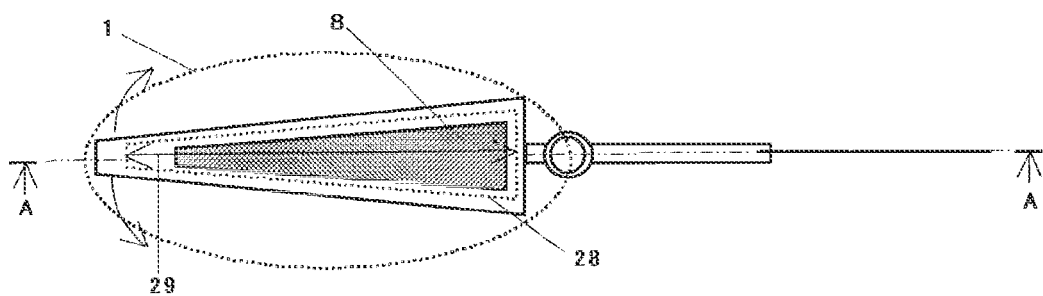
FIG. 2B is a schematic plan view of the related art.

Hereinafter, preferred embodiments of the invention will be described in detail by referring to the accompanying drawings.

Furthermore, in the specification and the drawings, the same reference numerals will be given to the components having substantially the same functional configurations, and the repetitive description thereof will be omitted.

In the description of the above-described related art and the description of the invention, the correlation between the components denoted by the same reference numerals does not indicate that the configurations and the functions thereof are the same as each other, but merely indicates, for example, a partial correlation in function or general designation. Even when the specific configurations or functions are different from each other, the same reference numerals may not be given thereto.

First Embodiment

Hereinafter, a first embodiment of the invention will be described by referring to FIG. 8.

A continuous atmospheric horizontal dustfall flux measurement device of the embodiment includes a dust sampling port 1, a suction pipe 5, a continuous dust amount measurement device 6, a blower or a compressor 7, and an exhaust port 8. External air or dustfall in the external air flows into the dust sampling port. The dust sampling port 1 is connected to the suction pipe 5 at the suction port 9. A part of an atmosphere and a part or all of the dustfall inside the dust sampling port 1 are introduced into the continuous dust amount measurement device 6 through the suction pipe 5. The continuous dust amount measurement device 6 continuously measures the dustfall amount. The atmosphere and a part or all of the dustfall passing through the measurement device are suctioned by the blower or the compressor 7 and are discharged to the outside of the system from the exhaust port 8. When the blower or the compressor 7 and the exhaust port 8 are not connected to each other in series, an air pipe 26 may be provided to connect the components to each other. Further, when the continuous dust amount measurement device 6 or the blower or the compressor 7 is not designed to have weather resistance, a casing 12 may be provided so as to accommodate such a device therein.

(Dust Sampling Port 1)

The dust sampling port 1 will be described by referring to FIGS. 9A to 9D and FIGS. 10A to 10C. The dust sampling port 1 includes a partition plate 4, a ceiling plate 3, and a side wall 2 provided with the external air inlet 10.

(Side Wall 2 of Dust Sampling Port 1)

The side wall 2 is a substantially conical (trumpet-shaped) plate of which the upper and lower ends are opened about the center axis corresponding to the vertical direction. The side wall 2 has a shape which is widened upward. Typically, the side wall 2 has a configuration in which a portion corresponding to a side surface of a truncated cone having a center axis corresponding to a vertical line is formed as a plate. The shapes of the upper and lower bottoms of the truncated cone may be a circular shape or a shape which is similar to a circular shape such as a regular polygon having at least four or more apexes. For example, when the upper and lower bottoms have a circular shape, the shape of the side wall 2 becomes a side surface of a circular truncated cone. Further, the horizontal cross-section of an arbitrary height of a space surrounded by the side wall 2 is a circular shape or a shape similar to a circular shape such as a regular polygon. Furthermore, the center of the horizontal cross-section or the centroid is positioned on the same vertical line at all times. The cross-sectional area of the horizontal cross-section gradually increases from the lower end of the circular truncated cone toward the upper end thereof.

Furthermore, a protrusion (for example, a head of a fixed bolt) or an opening (for example, a port or the like) sufficiently smaller than the area of the plate may be present on the plate surface.

It is desirable that the area of the opening or the protrusion be, for example, the cross-sectional area less than 10% of the area of the plate. Likewise, in the embodiment, since the substantially conical side wall 2 is employed, the dustfall trapping efficiency of the dust sampling port 1 may be less dependent on the direction of the wind. From this viewpoint, it is desirable that the side wall 2 have an axisymmetric shape. However, due to convenience in processing, the horizontal cross-section may be a shape similar to a circular shape such as a regular polygon or a shape in which anisotropy within a horizontal plane is comparatively small. For example, specifically, the horizontal cross-section may have a regular hexagonal shape, a regular octagonal shape, a regular dodecagonal shape, a hexadecagonal shape, or the like, and the anisotropy decreases as the number of angles of the horizontal cross-section increases. The horizontal cross-section of the side wall 2 may not be necessarily a regular polygonal shape as long as the shape may maintain low anisotropy. For example, the anisotropy may be limited to a constant range as long as a shape is provided in which the outer edge of the horizontal cross-section is included in a circular ring with a constant width. For example, a circular ring is defined in which the minimal radius Rmin becomes 0.6×Max when the maximal radius from the center point is denoted by Rmax, and a shape may be provided in which the outer edge of the horizontal cross-section is included in the circular ring. Further, the shape of the outer edge of the horizontal cross-section may be defined by using the circular ring having the minimal radius of 0.8×MR.

The open portion of the lower end of the side wall 2 is the air port 9, and is connected to the air pipe 5. A part of the dustfall flowing into the dust sampling port 1 sinks along the slope of the side wall 2, reaches the air port 9, and is suctioned by the air pipe 5. It is desirable that the inclination of the side wall 2 be at least 45° or more and desirably 65° or more with respect to the horizontal plane. In this case, when the average inclination of the air pipe 5 with respect to the horizontal plane is sufficiently large and dustfall sinks in the dust sampling port 1, most of the dustfall is suctioned to the air pipe 5 without adhering to the side wall 2. On the other hand, when the inclination with respect to the horizontal plane is drastically large, the axial length of the dust sampling port 1 becomes longer and the surface area increases, which is advantageous from the viewpoint of the adherence of the dustfall to the wall surface. Thus, it is desirable that the inclination of the side wall 2 with respect to the horizontal plane be 85° or less.

It is desirable that the thickness of the side wall 2 be at least 10 mm or less and desirably 3 mm or less. In this case, the air passage resistance of the external air inlet 10 provided in the side wall 2 is small, and the external air sufficiently flows into the dust sampling port 1. On the other hand, it is desirable that the thickness of the side wall 2 be 0.3 mm or more. In this case, it is possible to prevent a problem such as resonance when the side wall 2 is vibrated due to wind.

It is desirable that the material of the inner surface of the side wall 2 be metal, glass, or ceramics in order to prevent the dustfall from adhering to the wall surface due to static electricity. Further, it is desirable that the inner surface of the side wall 2 be smooth in order to suppress the adherence of the dustfall. From this viewpoint, when the material of the inner surface of the side wall 2 is metal, stainless steel, aluminum, aluminum alloy, steel subjected to a corrosion preventing surface treatment such as zinc plating or chrome plating, copper, coppery alloy, magnesium alloy, titanium, titanium alloy, and the like may be used. Further, when ceramics is used for the inner surface of the side wall 2, china or stoneware may be used in order to prevent the dustfall from adhering to the inner surface of the side wall 2 due to moisture absorption to the inner surface. When glass is used for the inner surface of the side wall 2, soda glass, lead glass, or silica glass may be used.

Since the side wall 2 receives strong wind outdoors and is exposed to sunshine or rainfall, the side wall 2 needs to have strength and weather resistance. From this viewpoint, as the structure material of the side wall 2, metal such as steel, alloy steel, aluminum, aluminum alloy, copper, copper alloy, magnesium alloy, titanium, or titanium alloy, ceramics such as china or stoneware, glass such as soda glass, lead glass, or silica glass, or rigid synthetic resin such as rigid vinyl chloride or acrylic may be used.

A plurality of the external air inlets 10 as openings of the side wall 2 is provided at a constant height near the upper end of the side wall 2 so as to have the same shape and be disposed at the same interval in the circumferential direction. The upper end of the external air inlet 10 may be equal to the upper end of the side wall 2 or may a position lower than the upper end of the side wall 28. Since the height of the upper end of the external air inlet 10 is derived from the limitation in height of the lower end of the external air inlet 10 and the limitation in total area of the external air inlet 10 to be described later, the height of the upper end of the external air inlet 10 may be appropriately determined within the limitation range. It is desirable that the axial position of the lower end of the external air inlet 10 be in the distance within ⅕ of the height of the side wall 2 in the axial direction of the side wall 2 at the upper end of the side wall 2 in order to improve the dustfall trapping characteristics.

It is desirable that the shape of the external air inlet 10 be symmetrical in the circumferential direction in order to reduce the dependence of the dustfall trapping efficiency with respect to the direction of the wind, and a shape such as a circular shape, an oval shape, a rectangular shape, a trapezoid shape, or an isosceles triangular shape may be used. The external air inlets 10 need to be disposed at the same position (that is, the same height) in the axial direction of the side wall 2 and have the same shape in order to reduce the dependence of the dustfall trapping efficiency with respect to the direction of the wind.

The number of the external air inlets 10 needs to be four or more and desirably eight to thirty-six. This is because of the result of the examination performed by the inventor. When the angle formed between the direction of the wind and the vector projected to the horizontal plane of the vertical unit vector with respect to the opening of the external air inlet 10 is 35° or more, it is proved that the amount of the wind flowing into the dust sampling port 1 at the same wind speed drastically decreases so that the dustfall trapping efficiency is degraded. For this reason, when the number of the external air inlets 10 is three or less, the angle formed between the direction of the wind and the external air inlet 10 at a certain external air inlet 10 becomes 35° or more so that wind may be generated in the direction of drastically decreasing the dustfall trapping efficiency. As the number of the external air inlets 10 increases, the influence of the direction of the wind reduces.

However, as described below, there is a desirable maximum value in the maximum area of the external air inlet 10 and the trappable dustfall amount increases as the total area increases up to the maximum area. For this reason, the total area of the external air inlet 10 may be set to a condition approximate to the maximum area. It is desirable to chamfer the outer end surface of the external air inlet 10 so as to reduce a degradation of the dustfall sampling efficiency due to the separation of the introduced atmosphere.

(Ceiling Plate 3 of Dust Sampling Port 1)

The ceiling plate 3 is disposed so that the center axes of the ceiling plate 3 and the side wall 2 match each other. Furthermore, the center axis of the ceiling plate 3 is defined as an axis passing through the center point of the ceiling plate 3 and perpendicular to the ceiling plate 3. Further, the ceiling plate 3 is disposed so as to adhere to the upper end of the side wall 2. The diameter of the ceiling plate 3 needs to be larger than the diameter of the upper end of the side wall 2. The outer ceiling plate portion in relation to the upper end of the side wall 2 serves as a peak portion, and exhibits an effect of preventing raindrops from intruding into the dust sampling port 1 in the case of rain. As the diameter of the ceiling plate 3 extending from the upper end of the side wall 2 becomes larger, the effect of suppressing raindrops from intruding into the dust sampling port 1 becomes higher. However, the maximal diameter of the dustfall flowing into the dust sampling port becomes smaller as the diameter of the ceiling plate becomes larger. Therefore, the maximum value of the diameter of the ceiling plate needs to be determined on the basis of the following equation.

[radial length of peak portion of ceiling plate]<[representative wind speed of external air]/[free falling speed of dustfall which is desired to be trapped]×[axial length between lower surface of ceiling plate and lower end of external air inlet]

For example, when 200 μm or less of dustfall is desired to be trapped on the basis of the average weather condition in Japan, it is desirable that a difference between the diameter of the ceiling plate and the diameter of the upper end of the side wall (the length of the peak portion) be from 50 mm to 200 mm. For example, when the representative wind speed of the external air is 2 m/s or more, the free falling speed of the dustfall designed to be trapped is 0.5 m/s, and the axial length between the lower surface of the ceiling plate and the lower end of the external air inlet is 0.01 m, if the equation is applied, the length along the radial direction of the peak portion of the ceiling plate may be set to 0.04 m, that is, the difference between the diameter of the ceiling plate and the diameter of the upper end of the side wall may be set to 80 mm.

Further, when the horizontal cross-section of the side wall 2 has a shape other than a circular shape, for example, a regular polygonal shape, the diameter of the circumscribed circle of the cross-section of the side wall at the upper end of the side wall may be regarded as the diameter of the upper end of the side wall 2. Furthermore, when the ceiling plate 3 has a shape other than a circular shape, for example, a regular polygonal shape, the diameter of the inscribed circle of the ceiling plate 3 may be regarded as the diameter of the ceiling plate 3.

The ceiling plate 3 needs to be a substantial disk in order to reduce the dependency with respect to the direction of the wind. The "substantial disk" indicates a structure in which the ceiling plate within the horizontal plane has small anisotropy and is thin. Specifically, it is desirable that the ceiling plate 3 be a disk. However, a shape similar to a circular shape such as a regular polygon having at least four or more apexes may be employed when convenience in processing or the like is considered. Further, the ceiling plate may be formed in a circular dome shape having a gentle inclination (that is, thin in the vertical direction) in consideration of drainage performance on the ceiling plate in the case of rainfall. For example, a circular dome in which the maximum inclination of the dome is 10° or less may be applied. In the case of a structure in which the ceiling plate is thick in the vertical direction, it is not desirable in that the air resistance of the ceiling plate becomes larger so that the external air flowing into the dust sampling port is disturbed.

Further, as in the description of the cross-sectional shape of the side wall 2, the shape of the outer edge of the ceiling plate 3 may be defined so as to be included in a circular ring with a constant width. Even in this case, the diameter of the inscribed circle of the ceiling plate 3 may be regarded as the diameter of the ceiling plate 3.

The material of the ceiling plate may be any type so long as the material has strength capable of maintaining the structure outdoors and does not permit the permeation of rainwater. Specifically, the material applicable to the side wall 2 may be applied to the ceiling plate 3. Further, the end surface of the ceiling plate may have an acute angle or a streamline shape in order to reduce air resistance.

(Partition Plate of Dust Sampling Port)

The partition plate 4 comes into contact with the upper portion of the side wall 2 including the ceiling plate 3 and the upper end of the side wall 2, and the partition plates are disposed so that the end surfaces thereof come into contact with each other at the center axis of the dust sampling port 1. As a result, the upper portion inside the sampling port is divided into small areas 27 each having a fan-shaped horizontal cross-section and having the external air inlet 10 and a downward opening. The partition plates 4 are installed so that a plurality of the fan-shaped small areas 27 having the same cross-sectional shape is disposed in the circumferential direction of the dust sampling port.

Figure 10A:
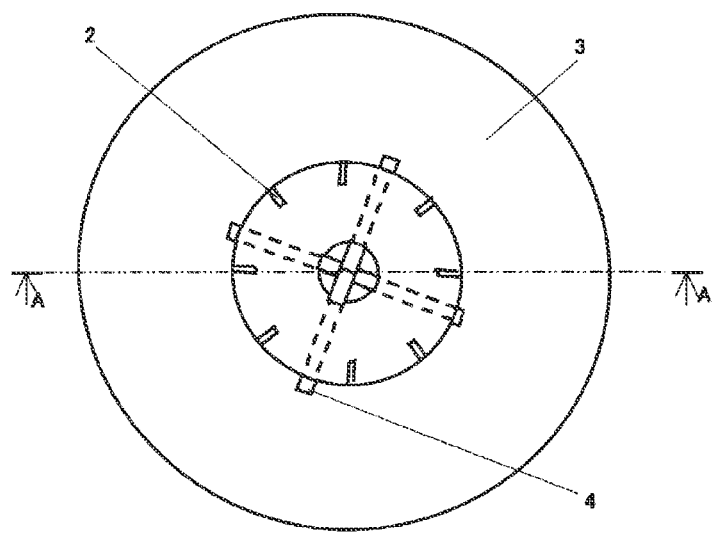
FIG. 10A is a schematic plan view illustrating a flow field inside the particle sampling port.
Figure 10B:
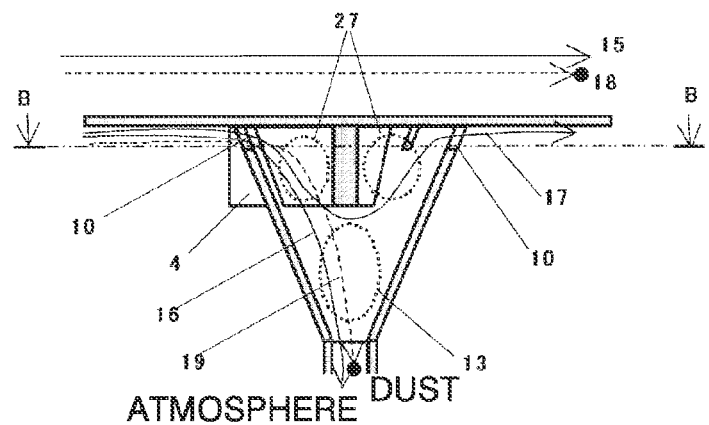
FIG. 10B is a schematic cross-section view taken along the plane A-A of the flow field inside the sampling port.
Figure 10C:
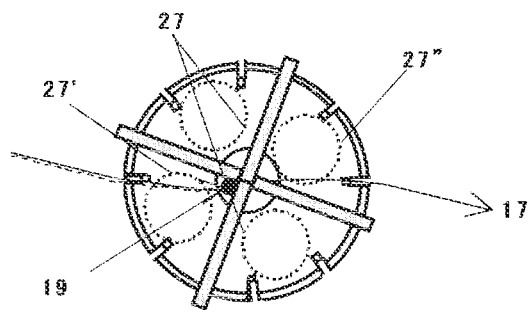
FIG. 10C is a schematic cross-sectional view taken along the plane B-B of the flow field inside the sampling port.

Here, when the number of the fan-shaped small areas 27 is four or more, most of the atmosphere flowing from the upstream external air inlet to the fan-shaped small area in the wind of the external air enters around the lower end of the partition plate 4 and passes through the wind reduction area 13 as shown in FIGS. 10A to 10C. On the other hand, when the number of the fan-shaped small areas 27 is three or less, most of the introduced atmosphere directly flows outward from the downstream external air inlet of the same fan-shaped small area. As described above, since the atmospheric dustfall is separated and condensed at the wind reduction area, there is a problem in that the ratio of the dustfall reaching the air port 9, that is, the dustfall trap ratio is low when the number of the fan-shaped small areas 27 is three or less. On the other hand, when the number of the fan-shaped small areas 27 is four or more, most of the atmosphere introduced from the external air inlet of the fan-shaped small area 27' where the atmosphere is introduced enters around the lower end of the partition plate 4, passes through the wind reduction area 13, and is discharged to the atmosphere from the fan-shaped small area 27" different from the fan-shaped small area 27 or is suctioned to the suction port. The inventor found that most of the atmospheric dustfall in the wind reduction area 13 is separated from the outward flowing atmosphere and is suctioned to the air port 9 in the meantime, so that high dustfall trapping efficiency is obtained. Therefore, the number of the fan-shaped small areas 27 needs to be four or more, and in order to realize this, the number of the partition plates needs to be four or more.

Figure 12:
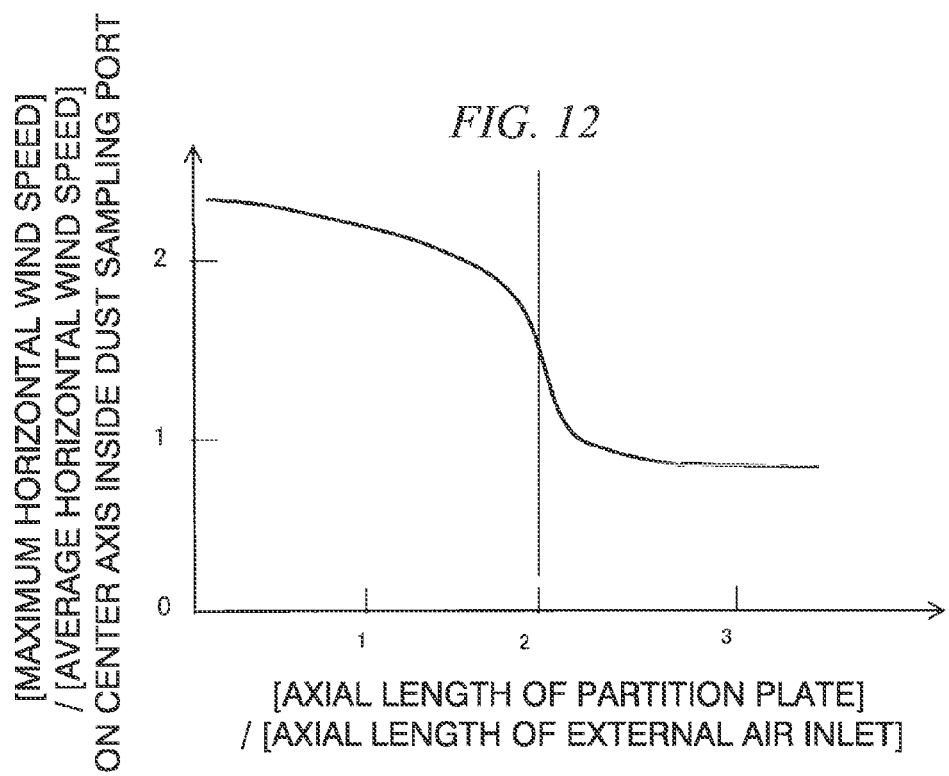
FIG. 12 is another schematic view illustrating the operation of the device according to the first embodiment of the invention.

Further, one or more external air inlets needs to be essentially present at the fan-shaped small area 27 so that the external air directly flows into the fan-shaped small area. Since there is a minimum value in the desirable cross-sectional area of the external air inlet 10, the total area obtained by adding the cross-sectional areas of all external air inlets 10 increases as the number of the fan-shaped small areas increases. As described below, since there is a maximum value having a desirable range in the total area of the external air inlet 10, there is a desirable maximum value in the number of the fan-shaped small areas, that is, the number of the partition plates. As a result of the examination of the inventor, it is desirable that the number of the fan-shaped small areas, that is, the number of the partition plates be sixteen or less. It is desirable that the axial length of the partition plate 4 be twice or more of the axial length of the external air inlet 10. In this case, as shown in FIG. 12 which is a result of the examination of the inventor, the maximum horizontal wind speed/the average horizontal wind speed on the center axis inside the dust sampling port 1 is not largely more than 1. That is, no blowing occurs in the horizontal direction inside the dustfall sampling port 1. Therefore, the dustfall trapping efficiency is high.

Figure 13:
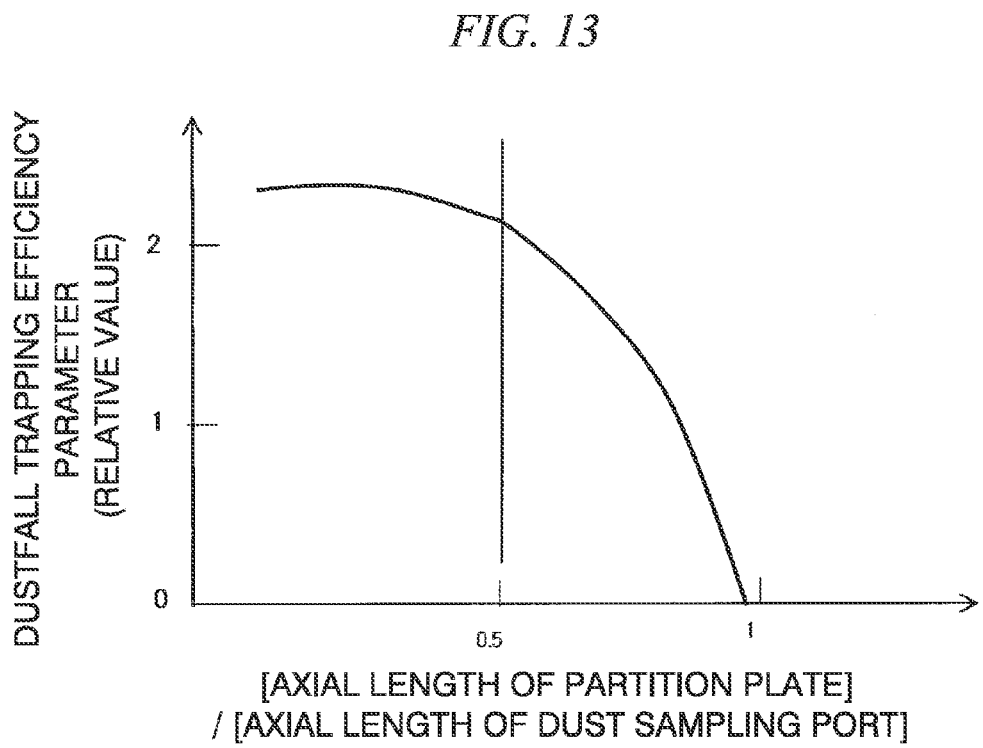
FIG. 13 is another schematic view illustrating the operation of the device according to the first embodiment of the invention.

Further, it is desirable that the axial length (height) of the partition plate 4 be equal to each partition plate 4 and be 0.5 times or less the axial length of the dust sampling port 1. As shown in FIG. 13 which is the inventor's search result, in the case of the value or more, the dustfall trapping efficiency parameter of the dust sampling port 1 to be described later becomes a sufficient value, and a sufficient dustfall trapping efficiency is obtained (as the dustfall trapping efficiency becomes larger, the dust trapping efficiency at the dust sampling port 1 becomes higher). In particular, when the axial length of the partition plate 4 is set to be extremely long to be equal to the axial length of the dust sampling port 1, the air passage resistance largely increases due to the partition plate 4 inside the dust sampling port 1 as another problem other than a degradation of the dustfall trapping efficiency parameter. Accordingly, the amount of the external air flowing into the dust sampling port extremely decreases, so that the dustfall trapping efficiency degrades.

Hereinafter, the value of [axial length of partition plate 4]/[axial length of dust sampling port 1] is denoted by L1. Further, the value of [axial length of partition plate 4]/[axial length of the external air inlet 10] is denoted by L2.

Further, referring to FIG. 13, the reason the tendency of the characteristic curve changes from the boundary when L1 is 0.5 will be described. The blowing inhibiting effect becomes higher as L2 becomes lager, whereas the area of the external air inlet may easily decrease and the dustfall trap amount may easily decrease. For this reason, L2 is designed to be about 2 as an appropriate lower limit value in many cases. In such a condition, the dustfall trapping efficiency parameter is substantially constant when L1 is 0.5 or less as shown in FIG. 13. In contrast, when L1 becomes more than 0.5, the dustfall trapping efficiency parameter abruptly reduces. The reason the dustfall trapping efficiency parameter reduces at L1 of 0.5 or more is because the space inside the dust sampling port becoming the wind reduction area 13 reduces. The reason the dustfall trapping efficiency parameter becomes constant at 0.5 or less is because of the following reasons.

When L1 is small, the space inside the dust sampling port which may become the wind reduction area 13 is wide, but there is a high wind speed area since the uniformity of the wind speed in the vertical direction is not sufficient. For this reason, the upper end of the wind reduction area 13 is fairly below the lower end of the partition plate 4. Since the wind speed in the vertical direction becomes uniform as L1 increases to approach 0.5, the gap between the upper end of the wind reduction area 13 and the partition plate 4 decreases. As a result, the upper end of the wind reduction area 13 becomes constant in the area where L1 is 0.5 or less. As a result, even when L2 is set to be smaller, the wind reduction area does not extend in the axial direction and the dustfall trapping efficiency parameter becomes a substantially constant value.

Furthermore, even when the wind speed in the vertical diction has a distribution in this area, the blowing in the horizontal direction does not occur in the case of the dust sampling port 1 where L2 is in the range of the appropriate condition. On the other hand, as described above, when L1 becomes more than 0.5 in FIG. 13, the dustfall maintenance parameter rapidly decreases as in the case of FIG. 13. Therefore, the value of 0.5 is important as a limit value in which L1 does not have an adverse influence on the dustfall trapping efficiency.

As a connection form between the partition plate 4 and the ceiling plate 3, the upper end surface of the partition plate 4 is connected to the lower side of the ceiling plate 3 without any gap formed therebetween or the partition plate 4 penetrates the ceiling plate 3 without any gap in the penetration portion. As a connection form between the side wall 2 and the ceiling plate 3, the outer end surface of the partition plate 4 is connected to the inner surface of the ceiling plate 2 without any gap formed therebetween or the partition plate 4 penetrates the side wall 2 without any gap formed in the penetration portion. Furthermore, in the connection form between the ceiling plate 3 and the partition plate 4 in FIGS. 9A to 9D, the upper end of the partition plate 4 is connected to the lower surface of the ceiling plate 3 without any gap formed therebetween. Further, in the connection form between the side wall 2 and the partition plate 4, the partition plate 4 penetrates the side wall 2 without any gap formed therebetween.

Further, in the fixation through such a connection, a method such as welding, adhering, or threading may be used. Further, a sealing material such as a silicon sealant or grease may be applied to the connection portion in order to suppress the inflow and outflow of the atmosphere by preventing a gap at the connection portion. As the material of the partition plate, any type may be used so long as the material may maintain its structure and has no air permeability and low adherability of dustfall. For example, the same material as that of the above-described side wall 2 may be used.

(Dustfall Trapping Mechanism of Dust Sampling Port 1)

A dustfall trapping mechanism inside the dust sampling port 1 of the embodiment will be described. In the embodiment, the atmospheric dustfall flowing from the external air inlet 10 flows into the wind reduction area 13 together with the atmosphere when the introduced atmosphere bypasses the partition plate 4 and passes the downside of the partition plate 4. When the dustfall flows into the wind reduction area 13, in the downward vertical direction due to the effect of changing the direction of the ambient atmospheric flow to the downward vertical direction or the effect of causing the dustfall particle to collide with the partition plate 4 the dustfall accelerates. For this reason, for example, a particularly large dustfall particle having a diameter of 100 μm or more directly falls to the air port 9, and is suctioned to the suction pipe. A part of the dustfall particle which is not particularly large freely falls while staying inside the wind reduction area 13, and reaches the air port 9 as in the larger dustfall particle so as to suctioned to the suction pipe. As described in the BSNE, which is the related art, the effect of the wind reduction area with respect to the trap of the dustfall is that the larger amount of dustfall is trapped downward compared to the case where the wind reduction occurs by extending the staying time of the dustfall inside the dust sampling port 1.

Next, the dustfall parameter contrived by the inventor will be defined by the following equation.

[dustfall trapping efficiency parameter]=[wind reduction area horizontal cross-sectional area 28]×[wind reduction area length 29]/[total area of external air inlet 10]$^2$ Here, the wind reduction area indicates an area where the wind speed of the atmosphere containing the dustfall flowing from the external air inlet 10 into the dust sampling port 1 at a certain flow wind speed is reduced. Further, the wind reduction area horizontal cross-sectional area 28 indicates a maximum value of the horizontal cross-section of the wind reduction area 13. Furthermore, the wind reduction area length 29 indicates a length of a line connecting from the boundary near the external air inlet 10 of the wind reduction area 13 to the suction port 10 (when exhaust to the external air is directly performed at the dust sampling port 1) or from the dust sampling port 1 to the exhaust port 8 (in the case of the BSNE) when exhaust to the external air is not directly performed or the downstream external air inlet 10 (in the case of the embodiment). In order to determine the specific position of the wind reduction area and the specific length of the wind reduction area, for example, the low wind speed area may be distinguished by obtaining a distribution of the wind speed inside the dust sampling port 1 using a flow meter disposed inside the dust sampling port 1.

Further, the physical meaning of the dustfall trapping efficiency parameter will be described. In the external air flowing into the dust sampling port 1 at a specific speed, the average staying time of the atmosphere and the atmospheric dustfall in the wind reduction area increases in proportion to [cross-sectional area of external air inlet 10]/[wind reduction area horizontal cross-sectional area 28]. Further, as the value of [wind reduction area length 29]/[cross-sectional area of external air inlet 10] becomes larger, the uniformity of the wind speed in the wind reduction area 13 more improves. That is, the effect of preventing a reduction in rapid blowing through only a part of the wind reduction area 13 from the boundary near the external air inlet 10 to the exhaust port 8 or the air port 10 becomes higher as the value of [wind reduction area length 29]/[cross-sectional area of external air inlet 10] becomes larger. Since the blowing phenomenon significantly shortens the average staying time of the atmospheric dustfall in the wind reduction area 13, the trapping efficiency is largely degraded. Therefore, the state where the dustfall parameter is large may be regarded as a state where the dustfall trapping efficiency due to the free falling dustfall becomes higher since the atmospheric dustfall usually stays in the wind reduction area 13 for a long time. Therefore, as the dustfall trapping efficiency parameter becomes larger, the dustfall trapping efficiency in the dust sampling port 1 becomes higher. That is, the dustfall trapping efficiency in the specific dust sampling port may be organized by using the dustfall trapping efficiency parameter.

A relation between the dustfall trapping parameter and the trapping efficiency of each trapping device will be more specifically described.

Figure 3:
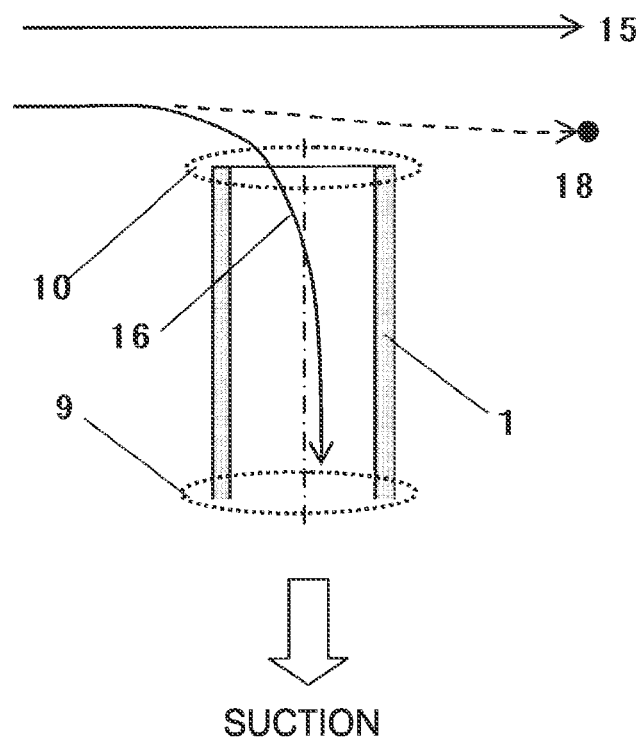
FIG. 3 is a schematic diagram of the related art.
Figure 4:
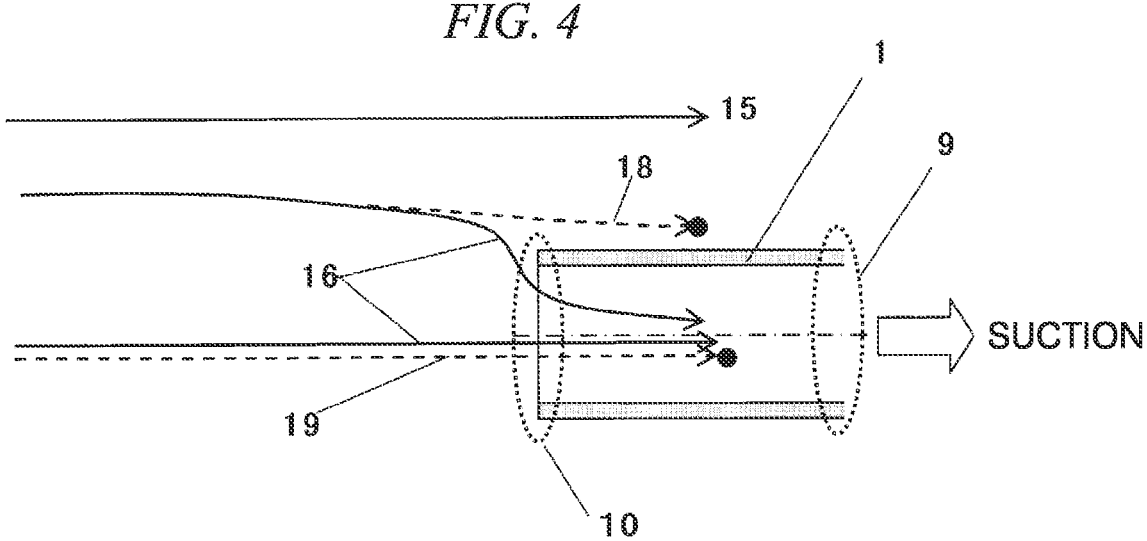
FIG. 4 is a schematic diagram of the related art.
Figure 11:
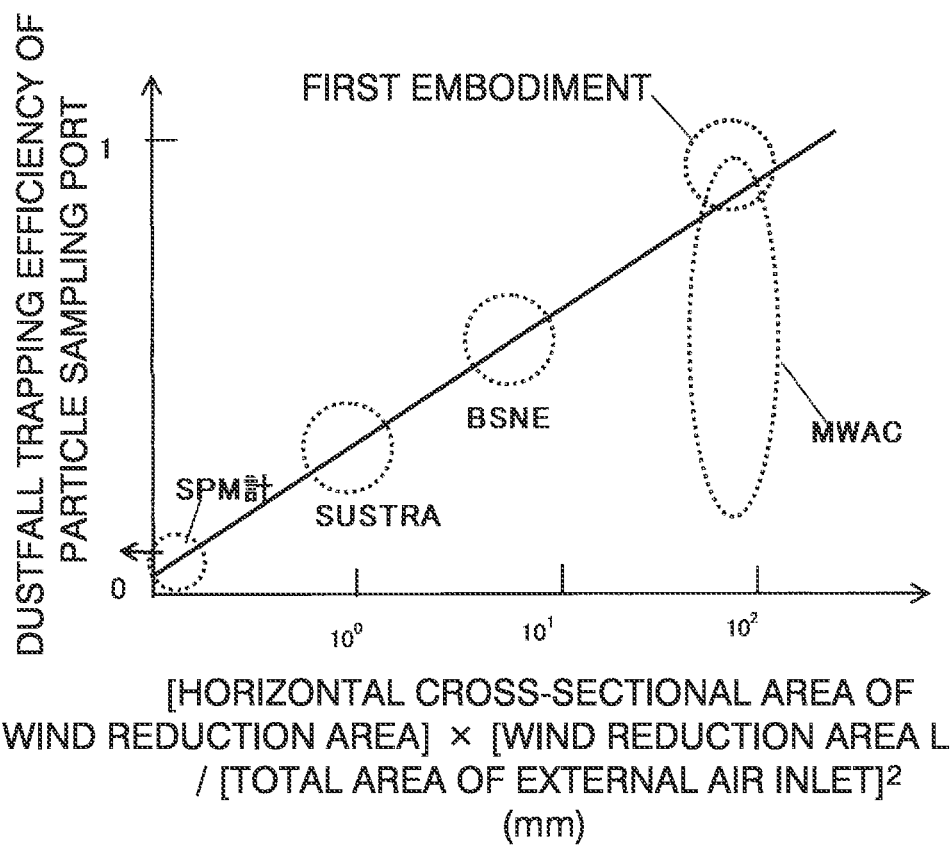
FIG. 11 is a schematic view illustrating an operation of the device according to the first embodiment of the invention.

In FIG. 11, the SPM meter corresponds to the case of using the dust sampling port shown in FIG. 3, and since the atmosphere flowing into the external air inlet 10 does not decelerate, there is no wind reduction area 13, and the volume of the wind reduction area is 0. At this time, since the large dustfall particle may not be suctioned at the dust sampling port, the dustfall trapping efficiency is remarkably low. In the dust sampling port 1 with a shape shown in FIGS. 6A and 6B and frequently used in the SPM meter shown in Patent Document 3, the wind reduction area 13 is formed below the conical disturbing plate 14. However, the area of the opening in the entire circumferential direction of the external air inlet is large, and the value of the dustfall trapping parameter is small. Further, since most of the atmosphere flowing from the external air inlet 10 into the dust sampling port 1 takes a flow passage 17 bypassing the periphery of the disturbing plate in the horizontal direction, the ratio of the atmosphere actually flowing into the wind reduction area is low. For this reason, even in the dust sampling port of FIGS. 6A and 6B, the dustfall trapping efficiency is small, whereby it is not suitable as the dustfall sampling port. In the SPM meter, since it is an object to trap only the SPM by separating the SPM from the large dustfall which may fall freely in the atmosphere, it is natural that the dustfall trapping efficiency of the dust sampling port 1 is low in the SPM meter.

Further, since the BSNE or the SUSTRA is a device that is designed to trap the dustfall, the device has the wind reduction area. However, in such a device, since the area of the external air inlet is large with respect to the volume of the wind reduction area, the dustfall trapping efficiency is low.

The MWAC may indicate that the value of the dustfall trapping efficiency parameter is comparatively large and at this time, the value of the dustfall trapping efficiency is high. However, the MWAC has a large defect in which the dependency of the dustfall trapping efficiency with respect to the wind direction of the external air is extremely strong. This defect is caused by the following reason. Since the vicinity of the opening of the external air inlet 10 of the MWAC is formed in a direct pipe, the atmosphere flowing into the external air inlet needs to have the axial speed of the direct pipe immediately after it flows thereinto. For this reason, when the axial direction of the external air inlet 10 is different from the wind direction of the external air, the flow resistance increases due to the abrupt change in direction of the atmosphere in the external air inlet 10, the inflow amount of the external air decreases, and the flow of the dustfall in the external air may not follow the abrupt change in direction of the inflow atmosphere, so that the amount of the dustfall flowing into the external air inlet 10 decreases. For this reason, in the MWAC, the dustfall trapping efficiency largely changes in accordance with the wind direction. In the MWAC, only when the wind direction of the external air is equal to the direction of the external air inlet, the dustfall trapping efficiency is high.

In the embodiment, since the external air inlets 10 are intermittently present in the circumferential direction of the dust sampling port 1, the value of the dustfall trapping efficiency parameter may be set to be larger than that of the device of the related art. When there is a need to obtain the maximum efficiency of the MWAC and the dustfall trapping efficiency, the value of the dustfall trapping efficiency parameter may be set to about 100 [1/mm]. This corresponds to a case where eight external air inlets 10 with a width of 3 mm and a height of 7 mm are provided at the upper end of, for example, an available trumpet-shaped reducer with an upper end diameter of 45 mm and a height of 60 mm. The dimensions of the trumpet-shaped reducer and the external air inlet 10 may be appropriately set so as to satisfy the condition necessary for the dustfall trap parameter.

Further, in the embodiment, most of the surface of the dust sampling port 1 is not opened. For this reason, compared to the other type in which the opening is large, the dust sampling port 1 of the embodiment has a large air resistance with respect to the ambient atmosphere. For this reason, a large negative pressure is generated at the surface of the dust sampling port 1 in the downward wind direction. As a result, a force is exerted on the external air inlet 10 in the downward wind direction so that the atmosphere inside the dust sampling port 1 is suctioned to flow outward. For this reason, even when the external air inlet 10 is relatively small and there is a difference between the direction of the external air inlet and the wind direction of the external air, the ventilation of the dust sampling port 1 is not particularly degraded. For example, even in the MWAC, although the opening area of the atmosphere inlet 10 is comparatively small, in the case of the device, a particular pressure reduction condition does not occur in the vicinity of the exhaust port 8 in the downward wind direction. For this reason, the ventilation of the dust sampling port 1 may be expected only by the effect of making the external air flow into the external air inlet 10 on the basis of the inertia of the flow of the external air. For this reason, in the MWAC, the ventilation efficiency of the dust sampling port 1 is easily degraded, which corresponds to a large factor of degrading the dustfall trapping efficiency.

In the embodiment, in order to continuously measure the amount of the trapped dustfall, the atmosphere inside the dust sampling port is suctioned from the narrow suction port 9. The reason the suction is performed is as below. When the suction is performed from the narrow suction port, the atmosphere containing the dustfall is collected at a narrow cross-sectional area, so that the space density of the dustfall or the dustfall flux increases, thereby highly precisely measuring the minute dustfall amount.

The minute dustfall amount measurement is an essentially required technique in the continuous dustfall amount measurement device which needs to measure the amount of the dustfall for a short period. Due to the suction, the dustfall trapping efficiency may be advantageously or disadvantageously influenced. First, as an advantage of performing the suction, the dustfall trapping efficiency may be higher than that of a simple trap such as a BSNE where the suction is not performed. For example, if the suction of the embodiment is performed even when the wind speed of the external air is low, a constant amount of the dustfall may be trapped. In such a case, in the BSNE, since the wind speed is low, the amount of the dustfall flowing into the dust sampling port is small, so that the dustfall trapping amount reduces. On the other hand, as a disadvantage of performing the suction, from the viewpoint of understanding the horizontal flux of the dustfall, when the dustfall trapping amount using the suction at a low wind speed is large, the wind speed of the external air is not involved with the dustfall trapping amount, so that the precision reduces.

Therefore, in the embodiment, the suction is performed, but in consideration of the above-described disadvantage, the atmosphere suction amount at the suction port 9 needs to be smaller than the amount of the free inflow atmosphere due to the wind speed of the external air into the dust sampling port 1. That is, the atmosphere suctioning amount at the suction port 9 needs to be smaller than the atmosphere outflow amount at the external air inlet 10 in the downward wind direction. This condition may not be satisfied when no wind occurs during the suction.

However, in the wind speed of 1 m/s or less, which is generally regarded as no wind in the weather forecast, the horizontal flux of the dustfall is not a problem. When the wind speed is less than 1 m/s even in the BSNE, the direction of the external air inlet 10 does not follow the wind direction, so that the accurate horizontal dustfall flux may not be obtained. For example, when the suction amount is set so as to satisfy the suction amount condition at the condition in which the wind speed of the external air is 1 m/s, the horizontal flux of the dustfall may be measured without causing a practical problem. Specifically, the dust sampling port 1 with a specific shape is disposed in one flow passage such as a wind tunnel, and air is suctioned from the suction port 9 at a specific suction flow rate. At this time, the flow rate of the atmosphere flowing outward from the external air inlet 10 in the downward wind direction is measured. When the measurement value is converted into the flow rate, it is possible to determine whether the suction flow rate is suitable at the dust sampling port with such a shape.

(Continuous Dust Amount Measurement Device 6)

As the continuous dust amount measurement device 6, various available dust amount measurement devices may be used. When mass is measured as a dust amount, mass may be highly precisely measured by using an available β-ray absorbing mass measurement device capable of periodically replacing a dust trapping filter. When the qualitative density of the dust amount needs to be obtained as the dust amount, an available light transmission type particle concentration meter may be used. Furthermore, a low volume sampler may be applied as a persudo continuous dust amount measurement device on the condition in which the dust trapping filter is manually replaced frequently.

Strictly speaking, the atmosphere flowing into such a device contains a particle such as minute SPM other than the dustfall. In an environment in which the concentration of the mass of the SPM particles is sufficiently smaller than the concentration of the mass of the dustfall, the mass of the dust trapped in the trap container may be all regarded as the mass of the dustfall. Further, when the concentration of the mass of the SPM may not be ignored, for example, in the β-ray absorbing mass measurement device, the hole diameter of the dust trapping filter is set to be large, so that only the large dust (for example, a diameter of 10 μm or more) may be trapped. When the mass of the trapping material is measured using this method, only the mass of the dustfall may be measured.

The dust amount measurement value measured in time-series using the continuous dust amount measurement device 6 measuring the dust amount per unit time is displayed on a display device (not shown), is recorded in a recording device (not shown) so as to refer to the data later, or is transmitted to a remote receiving device using a transmission device (not shown). The related art may be used in any method. For example, a monitor may be used as the display device. A printer or a hard disk device may be used as the recording device. A computer connectable to a LAN may be used as a transmission device.

(Blower or Compressor 7)

As such a device, the related art may be directly used. For example, a centrifugal type blower or compressor, an axial flow type blower or compressor, or a volume type blower or compressor may be used.

(Exhaust Port 8)

The exhaust port 8 is a portion that discharges the atmosphere, suctioned inside of the continuous horizontal dustfall flux measurement device of the embodiment, to the outside of the system. The exhaust port may be a simple pipe with an opening or may have a louver structure in order to improve weather resistance.

(Method of Calculating Horizontal Dustfall Amount Flux)

The horizontal dustfall amount flux value may be calculated by dividing the dustfall amount measured by the continuous dust amount measurement device 6 per unit time by the effective opening area of the external air inlet. In the embodiment, the effective opening area of the external air inlet is the sum of the area projected to the plane perpendicular to the wind direction in the opening area into which the external air flows in the external air inlet, and has an original value for the device. In order to specify the opening into which the external air flows, for example, the device is disposed inside the wind tunnel and measures the flow field near the dust sampling port 1 under a constant wind speed condition. Accordingly, it is possible to determine whether the external air flows into each external air inlet.

Further, generally, the average flow speed of the external air at the opening of the external air inlet becomes smaller than the wind speed of the external air due to the air resistance of the dust sampling port 1. As a result, the mass of the dustfall flowing into the dust sampling port 1 together with the external air also reduces compared to the case where the external air flows into the dust sampling port 1 at the wind speed of the external air. That is, the dustfall trapping efficiency at the dust sampling port is generally lower than 100%. Therefore, when calculating the horizontal dustfall amount flux, the horizontal dustfall amount flux value may be corrected by dividing the horizontal dustfall amount flux calculated in advance by the above-described method by the dustfall trapping efficiency obtained in advance. As a method of obtaining the dustfall trapping efficiency in advance, for example, the following method may be used. First, the device is disposed inside a wind tunnel, and a specific type of dustfall is discharged with a constant concentration from the upstream. At this time, the mass of the dustfall trapped by the device per unit time, the external air inlet effective opening area obtained by the above-described method, and the average value of the horizontal dustfall amount flux is obtained. By using the average value, the dustfall trapping efficiency is calculated in the following equation.

[dustfall trapping efficiency]=[mass of dustfall trapped by device per unit time]/([external air inlet effective opening area]×[average value of horizontal dustfall amount flux inside wind tunnel])

may be established.

The average value of the horizontal dustfall amount flux inside the wind tunnel may be obtained by the method or the like disclosed in Non-patent Document 2. Here, the "specific type" may be a mixture of a plurality of types of dustfall (which may be designated in advance), and a plurality of experiments may be performed for each type of dust. For example, a representative dust composition ratio at a measurement point may be simulated for experiment.

In the above-described calculation of the horizontal dustfall amount flux, a calculation device (not shown) may be disposed inside the device and b connected to a continuous dust amount measurement device through a data communication line. The dust amount measurement value using the continuous dust amount measurement device may be received by the calculation device. The calculation device may calculate and record the horizontal dustfall amount flux on the basis of the measurement value, and the horizontal dustfall amount flux may be calculated off-line later by using the dust amount measurement value of the continuous dust amount measurement device.

Further, in the embodiment, the amount of the trapped dustfall is proportional to the horizontal flux of the amount of the dustfall in the external air regardless of the wind speed of the external air. Therefore, when the absolute value of the horizontal dustfall amount flux is not needed for the purpose of managing the tendency of the horizontal dustfall amount flux, the standard value of the dustfall amount measurement value in the device of the embodiment is determined in advance, and the relative horizontal dustfall flux may be obtained by dividing the dustfall amount measurement value obtained in time-series in the continuous dust amount measurement device of the embodiment by the standard value.

(Search for Dustfall Generation Source)

When the time-series measurement value of the horizontal dustfall amount flux is analyzed by the combination with the time-series actual measurement value of a weather condition such as wind, a dustfall generation source such as a farmland or a factory may be searched for. For example, it is supposed that the measurement value of the horizontal dustfall amount flux corresponds to the dustfall generated from the dustfall generation source existing in the upward wind direction at that time. It may be estimated that a main generation source is present at the horizontal dustfall flux measurement point in the dustfall generation source present in the upward wind direction of the wind when detecting the horizontal flux of the more horizontal dustfall.

Second Embodiment

Figure 14:
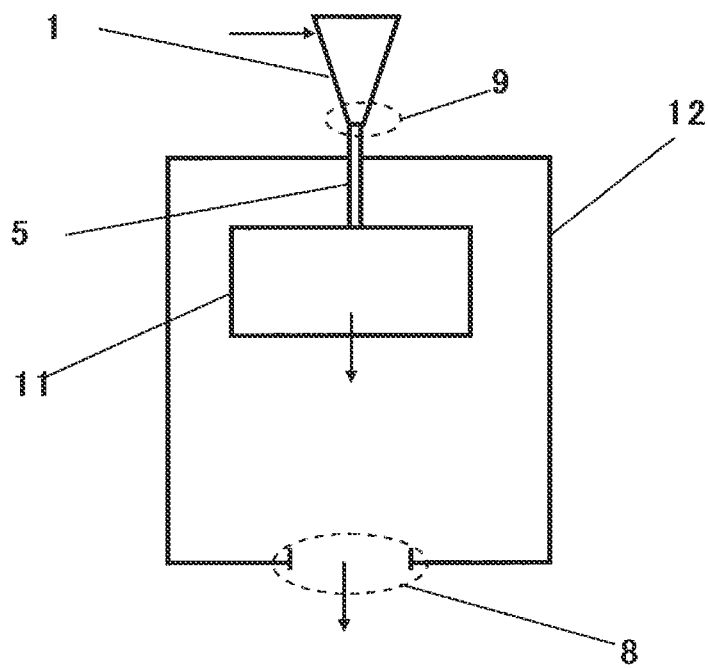
FIG. 14 is a schematic view illustrating a device according to a second embodiment of the invention.
Figure 15:
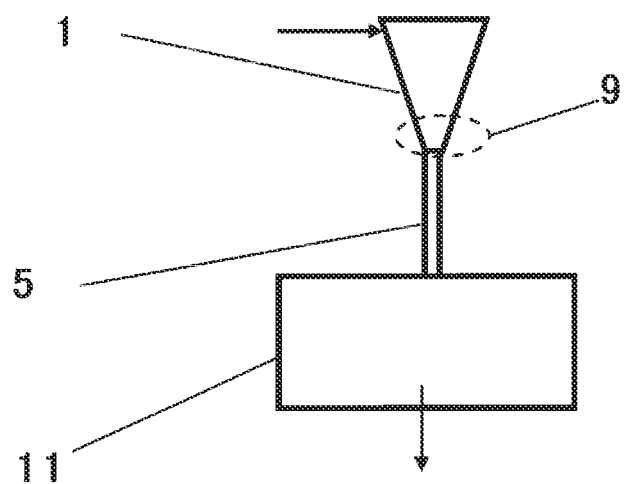
FIG. 15 is a schematic view illustrating a device according to a third embodiment of the invention.

Referring to FIG. 14, a second embodiment of the invention will be described. In the second embodiment, the particle counter 11 is used as the continuous dust amount measurement device. As the particle counter, an available particle counter may be used. Since most of the available particle counters include an air suctioning blower or compressor, the blower or the compressor is not particularly provided outside the particle counter 11 in FIG. 14. Further, since the particle counter generally includes an exhaust port, all atmosphere and a part or all of dust suctioned by the particle counter 11 is discharged to the inside of a protection casing 12 with weather resistance. The atmosphere and dust discharged to the inside of the protection casing naturally flows into the external air through the exhaust port 8 provided in the protection casing. Further, when the particle counter does not have weather resistance or originally does not require the weather resistance, a structure (a third embodiment of the invention) shown in FIG. 15 without the protection casing 12 may be adopted.

The advantage obtained when using the particle counter as the continuous dust amount measurement device is as below. As the first advantage, the particle counter may measure the amount of dust (the number of dusts) in a flowing state without trapping the dust in a non-contact manner. For this reason, even when a minute water drop such as mist intrudes into the continuous dust amount measurement device, a failure or a measurement error is not easily caused due to a problem in which water intrudes into the units inside the continuous dust amount measurement device. From this viewpoint, a remarkable effect of an available sheath air type particle counter is obtained which has an effect in which a part of the suctioned atmosphere is circulated inside the device and the units inside the device are sealed from the suctioned atmosphere.

As a second advantage, since the particle counter has a comparatively simple structure, and the number of movable portions other than the blower or the compressor is comparatively small, a decrease in size of the device is easy and hence the protection casing 12 may be decreased in size. When the protection casing is large, the flow of the external air largely drifts due to the resistance of the casing in the range of a distance substantially equal to the representative length of the casing from the casing. When the drifting area is provided with the dust sampling port 1, the dust trapping efficiency largely changes due to the influence of the drift compared to the case where there is no drift. For this reason, the dust sampling port 1 needs to be provided to substantially have the representative length of the protection casing 12 and be separated from the protection casing 12. In the case of a large casing, the suction pipe 5 needs to be provided to be long depending on each situation. When the suction pipe 5 is long, there is a problem in that the blower or the compressor increases in size due to an increase in size of the air suctioning resistance or the measurement is adversely influenced by the attachment of dust particles to the inner surface of the suction pipe. In the case of using the particle counter, since the representative dimension of the casing becomes smaller, the length of the suction pipe 5 may be made small, which is advantageous in such a problem.

As a third advantage, the schematic dimension of the detected particle may be estimated from the magnitude of the scattering (or reflecting) amount of the irradiation light due to the dust particle when detecting each dust using the particle counter. In the embodiment, only the dustfall which is a comparatively large particle is set as the measurement subject. For this reason, since the device is set so as to detect only the particle having a large irradiation light scattering amount (for example, a diameter of 10 μm or more), only the dustfall may be counted by using the particle counter.

Fourth Embodiment

Figure 16:
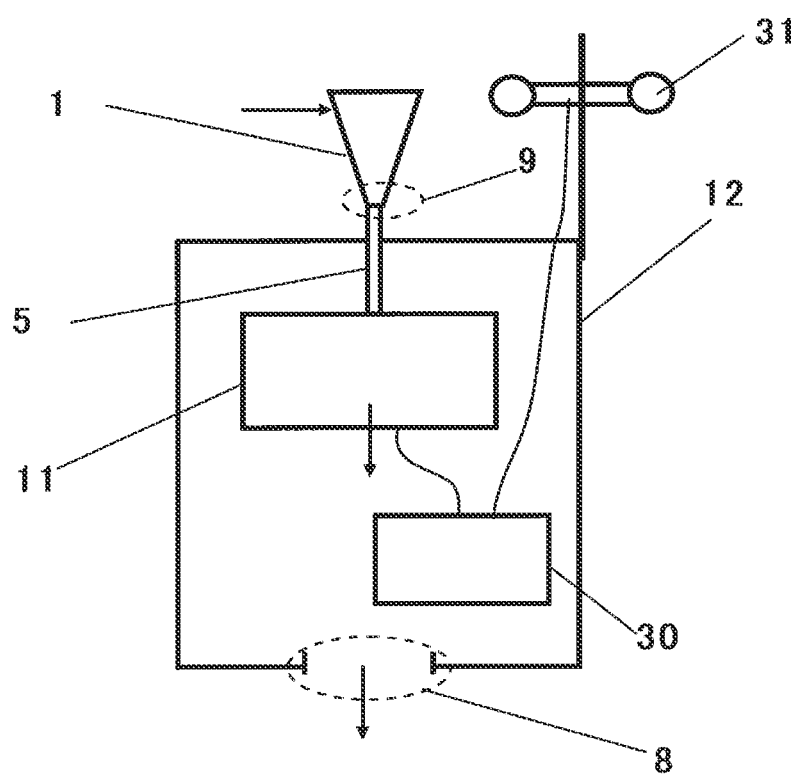
FIG. 16 is a schematic view illustrating a device according to a fourth embodiment of the invention.

Referring to FIG. 16, a fourth embodiment of the invention will be described. In FIG. 16, an aerovane 31 and a calculation device 30 are added to the device of the second embodiment shown in FIG. 14. The aerovane 31 may be attached to the vicinity of the dust sampling port 1. The aerovane 31 may be directly attached to the casing, or may be installed on an independent trestle. As the aerovane 31, an available cup aerovane or a propeller aerovane may be used. Since the dust sampling port 1 of the embodiment has a substantially axisymmetric shape, the wind direction dependency of the dustfall trapping efficiency is small. For this reason, the wind direction measurement function usually provided in the aerovane 31 is not essentially required. The average wind speed data measured by the aerovane is transmitted to the recording device 30 connected to the aerovane. Further, the calculation device 30 is also connected to the particle counter 11 as the continuous dust amount measurement device, and the momentary dust amount data measured at the particle counter 11 is transmitted to the calculation device 30. As the calculation device 30, for example, an available personal computer may be used.

The momentary dust amount data and the average wind speed data per unit time simultaneously received by the calculation device 30 are converted into the atmospheric momentary dustfall concentration (the momentary external air dustfall concentration) by causing the calculation device 30 to perform the following equation (following equation (1)).

[momentary external air dustfall concentration]=[momentary dustfall measurement value]/([average wind speed measurement value]×[effective external air inlet area])    (1)

Here, "momentary" indicates an average of a continuous measurement value for a predetermined short time (for example, one minute or one hour), a calculation average of an intermittent measurement value for a predetermined short time, or a measurement value in the event of a certain event (for example, a clock activated at a predetermined cycle).

Further, here, the effective external air inlet area indicates the sum of the external air inlet area of a portion estimated as the contribution to the inflow of the external air in the external air inlet 10. This value may be obtained by dividing the flow rate of the atmosphere passing through the inside of the dust sampling port 1 obtained by an experiment using the flow meter by the wind speed of the external air. In order to obtain the wind speed of the external air of the portion estimated as the contribution to the inflow of the external air, the aerovane is disposed near each external air inlet, and the inflow amount of the external air from the external air inlet is measured for determination. The reason the concentration of the dustfall in the atmosphere may be calculated by the above-described equation is as below. In the first and second embodiments, the momentary dustfall amount measured in the continuous dust amount measurement device 6, that is, the dustfall amount measured per certain time is highly precisely correlated to the horizontal flux of the dustfall as described above. That is, since most of the dustfall flowing into the dust sampling port 1 may be suctioned to the continuous dust amount measurement device 6, the above-described calculation is effective.

In the case of the measurement using the fixed dust sampling port 1 of the related art, due to the reason of the dustfall trapping efficiency is low as in the SPM system or an influence affecting the dustfall trapping efficiency such as a change in wind direction and wind speed as in the MWAC, even when the concentration of the dustfall in the atmosphere is calculated by using the aerovane data in a method similar to the embodiment, high measurement precision may not be obtained. Further, when the concentration of the dustfall in the atmosphere needs to be highly precisely measured in the related art, for example, there is a need to control a complex control or a complex mechanism performing uniform suction in accordance with the wind direction and the wind speed of the external air. On the other hand, in the embodiment, the concentration of the dustfall in the atmosphere may be simply and highly precisely measured only by using the fixed dust sampling port 1, the air suction meter suctioning air at a constant flow rate, and a general aerovane.

The concentration of the dustfall in the atmosphere calculated in the calculation device 30 may be displayed by connecting the calculation device to an output device such as a monitor (not shown) or may be stored in a recording device by connecting the recording device (not shown) to the calculation device 30. The obtained concentration of the dustfall in the atmosphere may be used only to manage the tendency of the fixed point as the index of the density of the concentration of the dustfall in the atmosphere, or may be converted into the dustfall speed by multiplying the average falling speed of the dustfall obtained separately by the concentration of the dustfall in the atmosphere.

EXAMPLES

Example 1

Figure 8:
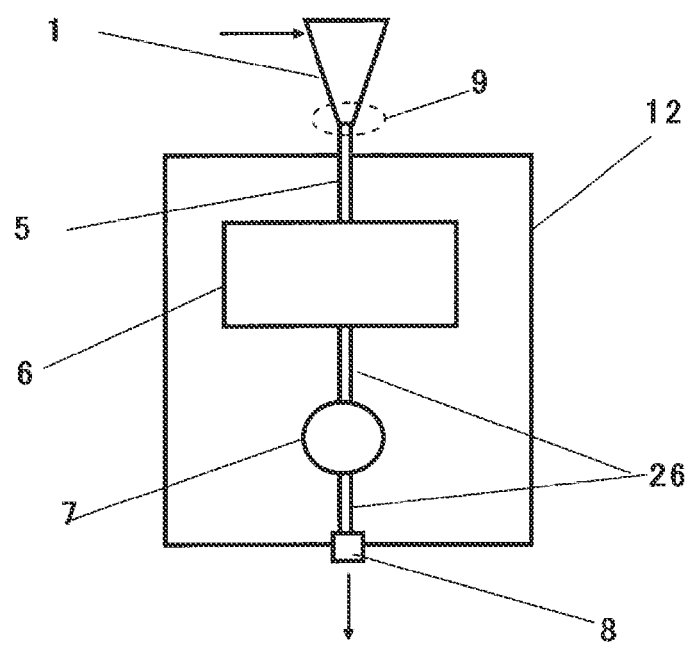
FIG. 8 is a schematic diagram of a device according to a first embodiment of the invention.
Figure 9A:
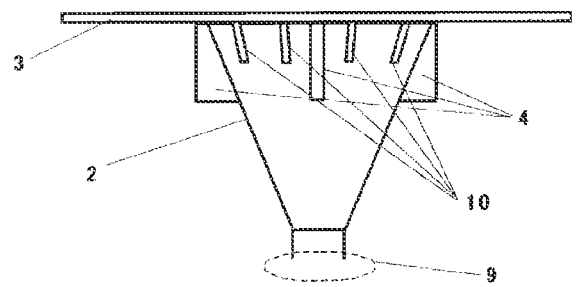
FIG. 9A is a schematic side view of a particle sampling port of the device.
Figure 9B:
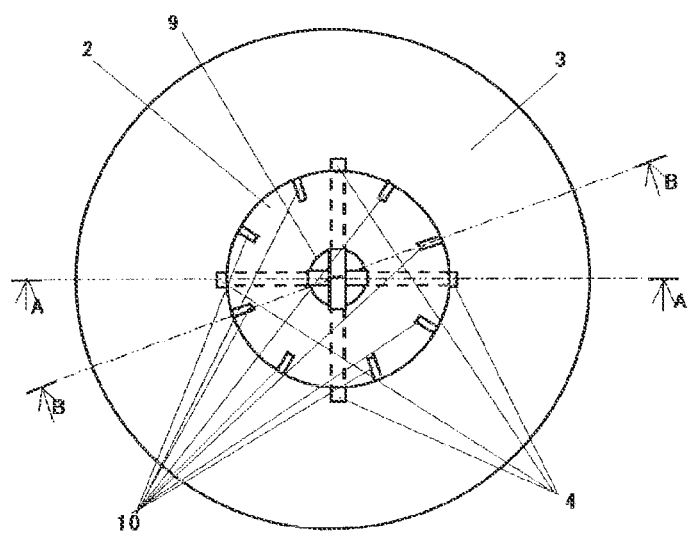
FIG. 9B is a schematic plan view of the particle sampling port of the device.
Figure 9C:
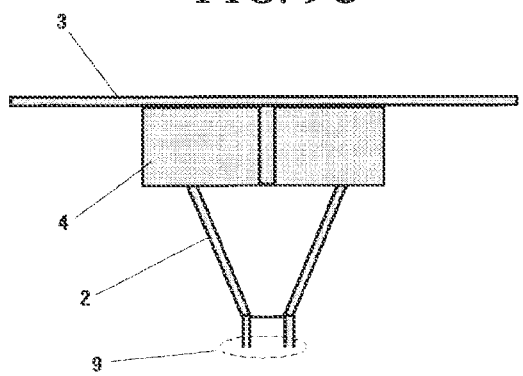
FIG. 9C is a schematic cross-sectional view taken along the plane A-A of the particle sampling port of the device.
Figure 9D:
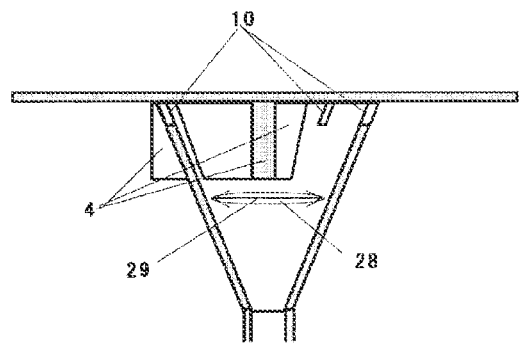
FIG. 9D is a schematic cross-sectional view taken along the plane B-B of the particle sampling port of the device.

The horizontal flux of the dustfall was continuously measured outdoors by using a device configured by applying the dust sampling port with the structure shown in FIGS. 9A to 9D to the configuration of FIG. 8.

As the side wall 2 of the dust sampling port 1, a reducer (with an outer diameter of an upper end of the reducer: 48 mm, an outer diameter of a lower end: 21.7 mm, and an axial length: 63 mm) of the stainless reducer 5K, 1½×½ according to JIS was used. In the pipe wall, the external air inlet 10 was formed by processing eight openings in the circumferential direction from the upper end of the side wall 2 so as to have a width of 3 mm and a height of 7 mm. In the same manner, four openings were processed in the circumferential direction from the upper end of the pipe wall so as to have a width of 4 mm and a depth of 25 mm. The partition plate 4 was formed by inserting four stainless steel plates with a width of 40 mm, a length of 24 mm, and a thickness of 4 mm into the openings. The partition plate was threaded into the ceiling plate 3 as a stainless disk with a diameter of 150 mm and a thickness of 2 mm. Therefore, a difference between the diameter of the ceiling plate 3 and the diameter of the upper end of the side wall 2 was 102 mm. An epoxy-based resinous adhesive was used for the connection between the ceiling plate 3 and the upper end of the side wall 2 and between the side wall 2 and the partition plate 4, so that they were bonded and sealed. A stainless pipe having a diameter of 1 inch was welded to the lower end of the side wall 2, that is, the suction port 9, and a stainless pipe having an outer diameter of 6 mm was welded to the lower end of the stainless pipe with a stainless reducer interposed therebetween, so that these stainless pipes were used as the suction pipe 5.

The available β-ray absorbing mass measurement device was used as the continuous dust amount measurement device 6, and the lower end of the suction pipe 5 was inserted and fixed into the inlet of the β-ray absorbing mass measurement device. A dust trapping filter was provided in the β-ray absorbing mass measurement device, and most of the dustfall in the atmosphere flowing into the β-ray absorbing measurement device was trapped in the trapping filter. An increasing amount of the mass measurement value per hour of the dustfall trapped on the trapping filter was transmitted to a personal computer (not shown) as a dustfall trapping value via a communication line. The dustfall trapping amount measurement value transmitted per hour was divided inside the personal computer by the time (one hour) and the previously registered external air inlet effective area, so that the horizontal flux measurement value of the dustfall was obtained at that time. This value was recorded and stored in a hard disk inside the personal computer. As the measurement time, the measurement receiving time recognized by the personal computer was applied by using a clock installed inside the personal computer. In this manner, the time-series data of the horizontal flux of the dustfall was recorded.

All atmosphere and minute dust passing through the trapping filter flowed outward from the exhaust port of the β-ray absorbing mass measurement device. The exhaust port was connected with an available diaphragm compressor 7 through an air pipe 26, and the diaphragm compressor 7 drove the air flow passing through the β-ray absorbing mass measurement device from the dust sampling port 1. Here, the suctioned flow rate was set to 2 L/min. The air pipe was connected with the exhaust port 8 as an opening provided with a louver taking a shelter from rain, and the atmosphere and a part of the dust suctioned into the device was discharged to the outside of the system from the exhaust port 8. The β-ray absorbing mass measurement device 6, the diaphragm compressor 7, and the air pipe 26 were accommodated inside a cubic casing 12 having weather resistance and formed of a galvanized steel sheet so that each side was 1 m. Further, the length of the upper exposed portion of the casing 12 of the suction pipe 5 was set to 700 mm. The weight of the device was 120 kg.

The method of the outdoor experiment is as below. The device was installed on a work desk positioned at the height of 5 m from the ground so as to be present in a position where no tall barrier was provided in the range of 200 m around the device by selecting a day with no rainfall, and continuous measurement was performed for twelve hours.

For comparison, a high volume sampler, capable of manually changing the direction of the air port and the air suction flow speed, and an aerovane were installed adjacent to the device, and the uniform suction was manually maintained during the experiment by using these. That is, the momentary measurement value of the aerovane was visually checked, and then an operation was normally performed in which the direction of the air port of the high volume sampler was manually made to match the wind direction measurement value and the air suction flow speed of the high volume sampler was made to match the wind speed measurement value. The dust trap filter of the high volume sampler was exchanged every hour so as to manually measure the mass thereof off-ray, whereby the dustfall trap mass per unit time was obtained. The value was converted into the horizontal flux of the dustfall by dividing the value by the time (one hour) and the suction port opening area of the high volume sampler. Furthermore, a preliminary survey was performed at the measurement value point of this Example, and it was confirmed in advance that the concentration of the mass of the SPM in the atmosphere at the corresponding point was sufficiently smaller than the concentration of the mass of the dustfall. Therefore, in this Example, the dust trap amount of each measurement device regarded as the dustfall trap amount.

As a result, the horizontal flux measurement value of the dustfall amount (mass) obtained by dividing the mass of the dustfall trapped per unit time in the device by the effective external air inlet area was 0.15 mg/m$^2$s in average. In contrast, a difference between the measurement value of the high volume sampler and the measurement value of the device at the same time was 0.02 mg/m$^2$s in average and the standard deviation thereof was small so as to be 0.01 mg/m$^2$s. Then, it was found that the device was able to highly precisely measure the horizontal flux of the dust amount (mass) as in the degree of the uniform suction.

Here, a method of calculating the effective opening area of the external air inlet will be described. In each of the plurality of external air inlets, the projection area of the plane perpendicular to the wind direction in the opening area into which the external air flowed was calculated, and the sum was defined as the effective opening area. In order to specify the opening into which the external air flows, the device was disposed inside the wind tunnel, wind with a constant wind speed was applied from the side surface thereof, and the wind directions near sixteen external air inlets were measured. The external air inlet having the direction in which the external air flowed into the dust sampling port in average was set to a subject for calculating the effective area. As a result of the measurement in various wind direction conditions, the effective opening area of the external air inlet was 1.6 times the opening area of each external air inlet in average.

This method is the most strictly precise method of calculating the effective opening area of the external air inlet. However, when the precision necessary for the horizontal component measurement value of the dustfall is low and good or the dustfall trapping efficiency is corrected by including an error caused when calculating the effective opening area, the simpler effective opening area may be defined. For example, it may be the sum of the area of the external air inlet present in average within the area of 70° from the center axis inside the plane perpendicular to the center axis in the external air inlet. This is because the external air further flows into the dust sampling port from the external air inlet when the line perpendicular to the wind direction in the opening surface is 35° or less as described above. Further, more simply, the area of the single external air inlet may be set as the effective opening area. Further, the projection area to the plane perpendicular to the wind direction of the area may be set as the effective opening area. Regarding the difference between the effective opening area values according to the definition, it is sufficient to clearly determine the definition of the effective opening area in advance since the values may be easily converted to each other.

Furthermore, the dust amount measurement using the uniform suction through the high volume sampler has high precision. However, there are problems in that the direction of the device and the suction flow rate need to be manually changed frequently from the device. For this reason, it is not desirable to apply the high volume sampler to the continuous measurement from the viewpoint of labor cost necessary for the measurement.

Comparative Example 1

Figure 6A:
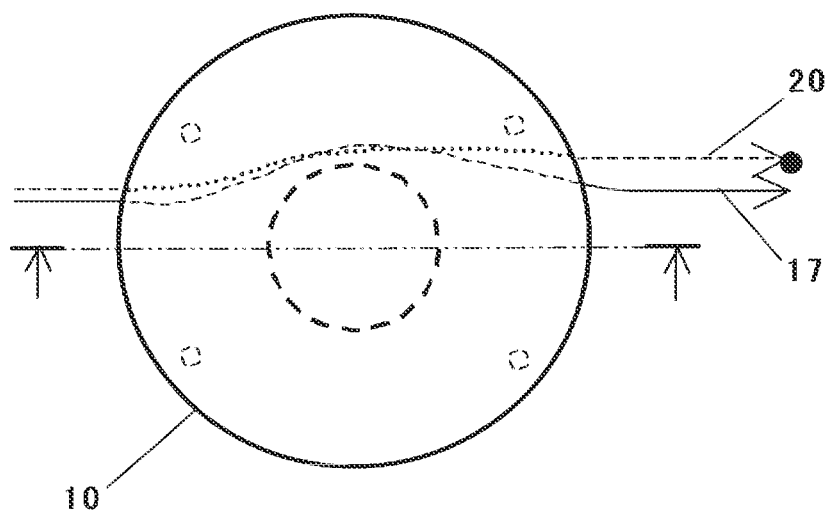
FIG. 6A is a schematic plan view of the related art.
Figure 6B:
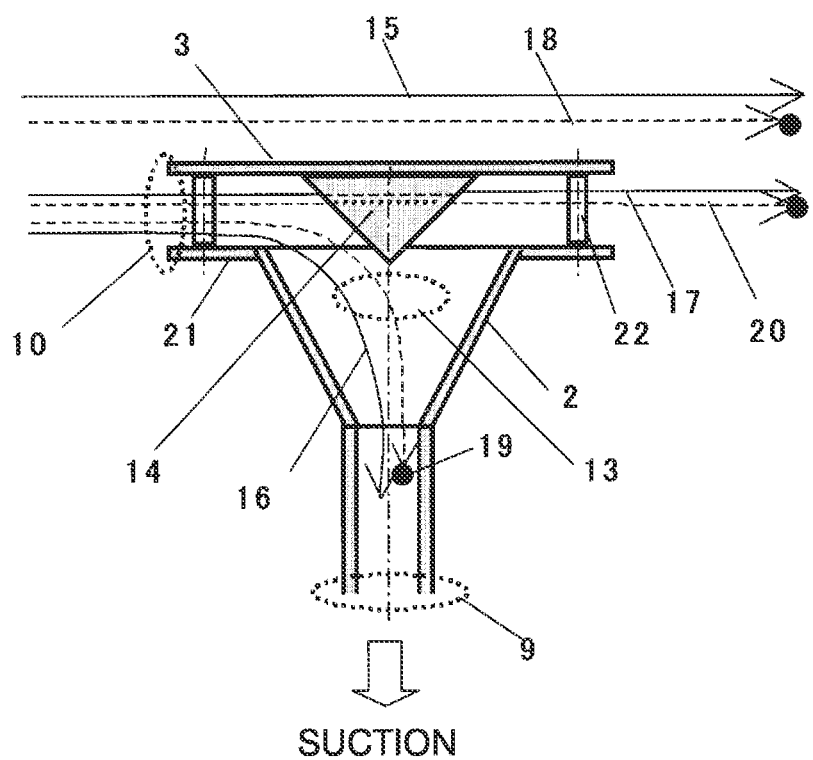
FIG. 6B is a schematic cross-sectional view of the related art.
Figure 7A:
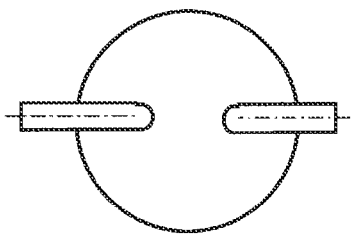
FIG. 7A is a schematic plan view of the related art.
Figure 7B:
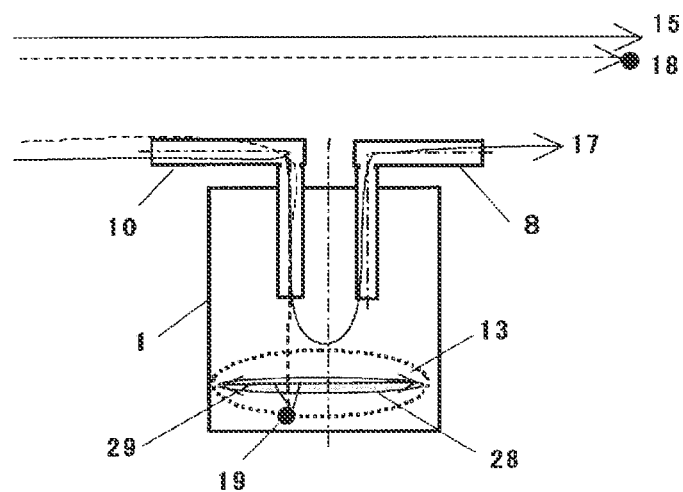
FIG. 7B is a schematic cross-sectional view of the related art.

An SPM measurement device was used including the ordinary dust sampling port 1 shown in FIGS. 6A to 6B and a cyclone was provided at the lower end of the dust sampling port 1 and separately trapping only the dustfall in the suctioned atmosphere in a trapping container. The SPM measurement device is an available beta-ray absorbing mass measurement-type continuous SPM measurement device. The experiment of Comparative Example 1 was performed in the state where the other conditions were the same as those of Example 1 except for the measurement device. The trapping container was replaced every hour to collect the trapped dustfall, and the mass thereof was measured off-line after the experiment. This value was set as the dustfall trapping mass measurement value for each hour. The dustfall trapping mass measurement value measured by the device was compared with the dustfall trapping mass measurement value of the high volume sampler performing uniform suction and corresponding to the comparative measurement device provided in parallel to the device. When comparing both measurement values, an influence of a difference in opening area of the external air inlet 10 between the device and the high volume sampler was reflected. When the dustfall trapping efficiency of the device was 100%, the dustfall trap mass measurement value using the high volume sampler was corrected so that the dustfall trap mass measurement value of the device was equal to the dustfall trap mass using the high volume sampler.

The dustfall mass measurement value per hour was measured by using the device of Comparative Example 1, and the horizontal dustfall flux calculation value was calculated as in Example 1. This result was compared with the measurement value of the dustfall trapping mass measurement value per hour using the high volume sampler and the horizontal dustfall flux calculation value calculated from the dustfall trapping mass measurement value. As a result, the value obtained in Comparative Example 1 was about 5% of the value obtained in the high volume sampler, and the correlation coefficient between both measurement values was low so as to be 0.4. Furthermore, when obtaining the effective opening area of the external air inlet, since this device had a single opening in the entire circumference thereof, the wind tunnel experiment was performed, and the portion introducing the external air in average into the external air inlet was obtained. The projection area of the plane perpendicular to the wind direction in the portion inside the external air inlet was set as the effective opening area. The configuration of the device of Comparative Example is substantially the same as that of Example 1 except for the shape of the dust sampling port 1. Further, as described above, in Example 1, the horizontal flux of the dustfall was able to be highly precisely measured. Therefore, it was found that the dustfall was able to be highly efficiently trapped when using the ordinary dust sampling port.

Example 2

As Example 2, a continuous measurement experiment was performed outdoors using the configuration of the device according to the second embodiment of the invention shown in FIG. 14. In this device, the same dust sampling port as that of Example 1 was used. However, in this device, the particle counter 11 was used instead of the continuous dust amount measurement device 6 and the blower or the compressor of Example 1.

The particle counter is of a sheath air type, and has a function of counting the number of particles in the atmosphere at three stages, a diameter of 10 μm or more, a diameter of 50 μm or more, and a diameter of 100 μm or more through standard glass correction particle conversion.

Here, the particle having a diameter more than 10 μm (including the particles having a diameter of 50 μm or more and a diameter of 100 μm or more) was regarded to correspond to the dustfall through standard glass correction particle conversion. The casing 12 having weather resistance was formed in a cubic box shape formed of a galvanized steel sheet so that each side was 300 m. The length of the upper exposed portion of the casing 12 of the suction pipe 5 was set to 100 mm.

According to the following method, the horizontal flux of the dustfall amount (that is, the number of the dustfalls of the device) was calculated. The number of the dustfalls per minute was counted by using the particle counter, and the result was transmitted to a personal computer (not shown) via a communication line every minute. In the PC, the number of the dustfalls was divided by the time (one minute) and the previously registered effective external air inlet opening area so as to be converted into the horizontal dustfall flux. The obtained horizontal dustfall flux was recorded and stored in the hard disk of the personal computer.

The weight of the device was 20 kg. The installation place of the device was the same as that of Example 1. The measurement period was set to one month in the weather condition including the time of the rain. Among these, the horizontal flux was measured for six hours at a specific day other than rainy days.

As a result, in the device, the number of the dustfalls having a diameter more than 10 μm, a diameter of 50 μm or more, and a diameter of 100 μm per hour had a strong positive correlation (a correlation coefficient of 0.7 or more) with respect to the horizontal flux of the dustfall amount (mass) measurement value of the uniform suction device for comparison. Here, the dustfall measurement number per hour was divided by the effective external air inlet area so as to be calculated as the horizontal flux of the dustfall amount (the number of dustfall particles). Therefore, the horizontal flux of the dustfall amount (the number of dustfall particles) measured and calculated by using the device had a high correlation with the horizontal flux of the dustfall amount (mass). It is generally known that the value of the horizontal flux of the dustfall amount (mass) measured and calculated by using the uniform suction device has high reliability. For this reason, according to this Example, the validity of the measurement precision of the horizontal dustfall amount flux using the device was confirmed.

Further, it was found that no failure occurred in the device including the case of rain and satisfactory weather resistance of the device was confirmed. In addition, it was found that the device was able to be automatically operated perfectly. It was found that there was a considerable rainfall amount for the measurement period and raindrops intruded into the device. However, in principle, no failure occurs in the particle counter unless a large amount of raindrop extremely intrudes into the device. In the experiment, no failure occurred even in the case of rainfall.

Example 3

In Example 2, the axial length (depth) of the external air inlet 10 was 7 mm, and the axial length of the partition plate 4 was 25 mm.

Therefore, the value L2 of [axial length of partition plate 4]/[axial length of external air inlet 10] was 25/7=3.57.

On the other hand, in Example 3, the device was configured such that the axial length of the partition plate 4 was set to 7 mm, and the other conditions were the same as those of Example 2. In the configuration of Example 3, L2 was 7/7=1.00, and this value was smaller than 2.

The device of Example 2 and the device of Example 3 were provided in parallel, and the dustfall measurement experiments were simultaneously performed. As a result, the device of Example 2 has higher dustfall trapping efficiency and less blowing inside the particle sampling port. The average number of the dustfalls per unit time and the horizontal flux value of the dustfall amount (the number of dustfall particles) calculated in the same manner as Example 3 were about 40% of the values of the device of Example 2. In addition to this, a plurality of experiments was performed, and when L2 is 2 or more as a result of the same calculation, the dustfall amount was further highly efficiently measured.

Example 4

In the device of Example 4, the axial length of the partition plate 4 was set to 80% (50.4 mm) of the axial length of the dust sampling port. The other conditions were set to be the same as those of Example 2, and the experiment was performed using the device provided in parallel to the device of Example 2 at the same time as that of the experiment of Example 2. As a result, the value of the dustfall trapping efficiency parameter was higher in Example 2, and the dustfall trapping efficiency was also higher. In the average number of the dustfalls per unit time and the horizontal flux value of the dustfall amount (the number of dustfall particles) calculated in the same manner as Example 2, the values of Example 4 were about 30% of the value of the device of Example 2.

Example 5

In the device of Example 5, in the state where a difference between the diameter of the ceiling plate 3 and the diameter of the upper end of the side wall 2 was set to 30 mm, and the other conditions were set to the same as those of Example 2, the experiment was performed at the same time as that of Example 2 by using the device provided in parallel to the device of Example 3. As a result, in a day in which the amount of the rainfall for each day was 20 mm and the maximal wind speed was 8 m/s, the raindrop intruding into the particle counter 11 was accumulated inside the particle counter and overflowed from the air flow passage. The raindrop intruded into the light receiving sensor of the particle counter so that a failure occurred. Furthermore, at the time at which no failure occurred, the average number of the dustfalls and the horizontal flux value of the dustfall amount (the number of dustfall particles) calculated in the same manner as Example 2 were equal to the values of the device of Example 2.

Example 6

The experiment was performed in the state where the dust sampling port 1 was set to be similar to Example 2, the dimensions was set to be twice, and the other conditions were the same as those of Example 2. As a result, the average number of the dustfalls per unit time and the horizontal flux value of the dustfall amount (the number of dustfall particles) calculated in the same manner as Example 2 was about four times those of the device of Example 2.

Example 7

Figure 5:
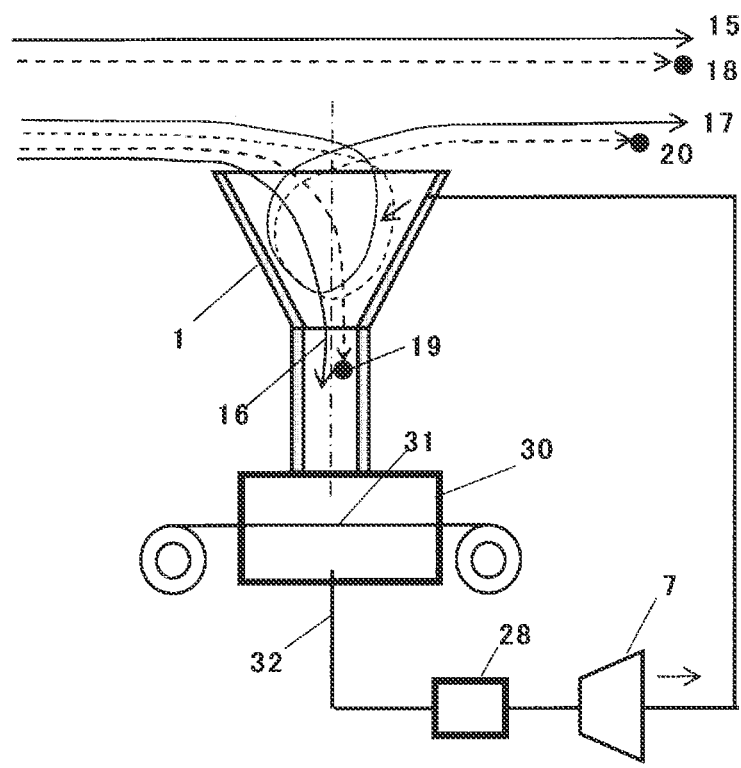
FIG. 5 is a schematic diagram of the related art.

The calculation device 30 as an available small personal computer was installed inside the casing 12 of the device of Example 2. Further, the cup aerovane 31 connected with the particle counter 11 via a communication line and including an analog voltage output terminal was prepared. The cup aerovane 31 was attached to the outside of the casing 12, and the analog voltage terminal of the aerovane 31 was connected to the small personal computer via a communication line. With this configuration, the momentary concentration of the dustfall in the external air was calculated and recorded using the small personal computer. Further, as a measurement device for comparison, the available continuous dust amount measurement device with a time shown in FIG. 5 was provided in parallel to the device, and the vertical flux of the dustfall was continuously measured at the same time. The experiment was performed by using the deice provided in parallel to the device of Example 2 at the same time as that of the experiment of Example 2 in the state where the other conditions were the same as those of Example 2.

A communication according to RS232C was used between the personal computer and the particle counter, and the number of particles per minute was transmitted every minute from the particle counter to the small personal computer via the communication line by the process of the calculation device inside the particle counter. The transmitted data was received by the process of the software provided in the small PC, and the number of particles per minute was recorded on the hard disk provided in the small personal computer together with the time at which the small personal computer received the data. As the time at which the personal computer received the data, the data of the clock built in the personal computer was used.

Further, the small personal computer was provided with an AD conversion input terminal, the terminal was connected to the analog voltage terminal of the aerovane via a coaxial cable, and the temporary voltage value of the analog terminal of the aerovane was converted by the small personal computer every second by the process of the software installed in the small personal computer. Then, a process of calculating the average wind speed value per unit time was performed by multiplying a predetermined conversion coefficient by the value.

Furthermore, the average wind speed value per second was averaged every minute by the process of the software installed in the small PC, and the result was recorded in the hard disk inside the small personal computer together with the time of the clock of the personal computer as the wind speed value data every minute. Next, the concentration of the dustfall in the external air was calculated by using Equation (1). That is, the number of the particles per minute recorded in the hard disk of the small personal computer was divided by the wind speed value every minute corresponding to the same time by the process of the software activated every minute by the small PC, and a process of multiplying a predetermined proportional coefficient based on Equation (1) was performed. The value of the result was recorded in the hard disk of the personal computer as the dustfall concentration value of the external air every minute at this time together with the time.

As a result, the average value for each hour of the concentration value of the dustfall in the external air using the device has a high correlation with a correlation coefficient of 0.7 with respect to the vertical dustfall flux measurement value for each hour of the continuous dust amount measurement device as a comparative measurement device. As described above, since the vertical dustfall flux is proportional to the concentration of the dustfall in the external air, it may be regarded that the vertical dustfall flux measurement value using the continuous dustfall amount measurement device corresponds to the density of the concentration of the dustfall in the momentary external air. Therefore, it was found that the density of the concentration of the dustfall in the momentary external air was able to be obtained by using the device.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

INDUSTRIAL APPLICABILITY

According to the invention, it is possible to continuously measure a horizontal flux of dustfall with high precision for a short period of one minute or so using a simple structure. Further, in addition to this, in one aspect of the invention, it is possible to realize an all-weather continuous atmospheric horizontal dustfall flux measurement device capable of performing measurement without any failure in the case of rain.

REFERENCE SIGNS LIST

1: dust sampling port
2: side wall
3: ceiling plate
4: partition plate
5: suction pipe
6: continuous dust amount measurement device
7: blower or compressor
8: exhaust port
9: suction port
10: external air inlet
11: particle counter
12: casing
13: wind reduction area
14: disturbing plate
15: atmospheric flow of external air
16: suctioned atmospheric flow
17: atmospheric flow passing into dust sampling port
18: dustfall in external air
19: trapped dustfall
20: dustfall passing into dust sampling port
21: bottom plate
22: support column
23: blade
24: rotary shaft
25: trap container
26: air pipe
27: fan-shaped small area
27': fan-shaped small area into which atmosphere flows
27": another fan-shaped small area
28: wind reduction area horizontal cross-sectional area
29: wind reduction area length
30: calculation device
31: aerovane
32: particle trap
33: metallic mesh

The invention claimed is:

1. A continuous atmospheric horizontal dustfall flux measurement apparatus comprising:
a dust sampling port that includes a ceiling plate, a side wall, and four or more partition plates;
a suction pipe;
a continuous dust amount measurement device that continuously measures a dust amount per unit time;
a blower or a compressor; and
an exhaust port,
wherein a flow passage is formed by sequentially connecting the dust sampling port, the suction pipe, the continuous dust amount measurement device, the blower or the compressor, and the exhaust port so that suctioned air flows in series,
wherein the side wall is a plate that has a vertical center axis and has a side surface with a substantially circular or polygonal truncated cone shape widened upward,
wherein the side wall includes a suction port which is formed at a lower end thereof and is connected to the suction pipe and an external air inlet which has four or more openings disposed at a same interval in the circumferential direction of the side wall and at a same height near the upper end thereof,
wherein the ceiling plate has a substantially disk shape, a diameter thereof is larger than a diameter of a horizontal cross-section of the upper end of the side wall, a center axis of the ceiling plate matches the center axis of the side wall, and the ceiling plate is connected to the upper end of the side wall so as to come into contact therewith,
wherein the four or more partition plates are four or more flat plates which are disposed in a vertical plane so as to divide a space surrounded by the side wall into fan-shaped areas with a same size in a horizontal cross-section, are connected to each other on the center axis, and have a same height, and
wherein the partition plates are connected to the side wall and to the ceiling plate without any gap therebetween.

2. The continuous atmospheric horizontal dustfall flux measurement apparatus according to claim 1,
wherein the ceiling plate includes a peak portion that extends outward in relation to the upper end of the side wall, and
wherein when Equation (1) is defined as:

((representative wind speed of external air)/(free falling speed of dustfall desired to be trapped))×(axial length between lower surface of ceiling plate and lower end of external air inlet), the length of the peak portion along the radial direction of the ceiling plate is smaller than the value of Equation (1).

3. The continuous atmospheric horizontal dustfall flux measurement apparatus according to claim 1,
wherein the continuous dust amount measurement device and the blower or the compressor constitute a particle counter.

4. The continuous atmospheric horizontal dustfall flux measurement apparatus according to claim 1, further comprising:
an aerovane that measures an average wind speed of external air per unit time;
a calculation device that receives the average wind speed value measured by the aerovane and a momentary dustfall amount measurement value measured by the continuous dust amount measurement device as an input value and calculates a momentary external air dustfall concentration on the basis of Equation (2) below:

(momentary external air dustfall concentration)=(momentary dustfall amount measurement value)/((average wind speed measurement value)×(effective opening area of external air inlet)) (2); and an output device that stores or displays the momentary external air dustfall concentration calculated by the calculation device.

5. The continuous atmospheric horizontal dustfall flux measurement apparatus according to claim 1,
wherein a length of each of the partition plates along an axial direction of the side wall is twice or more of a length of the external air inlet along the axial direction of the side wall.

6. The continuous atmospheric horizontal dustfall flux measurement apparatus according to claim 1,
wherein a length of each of the partition plates along an axial direction of the side wall is 0.5 times of a length of the dust sampling port along the axial direction.

7. The continuous atmospheric horizontal dustfall flux measurement apparatus according to claim 1,
wherein the blower or the compressor suctions a part or all of dustfall flowing into the dust sampling port along with air together with a part of the air inside the dust sampling port, introduces the dustfall and the air into the continuous dust amount measurement device through the suction pipe from the suction port, and discharges the suctioned air from the exhaust port.

8. A continuous atmospheric horizontal dustfall flux measurement method using the continuous atmospheric horizontal dustfall flux measurement apparatus according to claim 1, wherein a value obtained by dividing the amount of the dustfall trapped per unit time by the effective opening area of the external air inlet is calculated as the horizontal flux of the dustfall.

9. The continuous atmospheric horizontal dustfall flux measurement apparatus according to claim 2, wherein the continuous dust amount measurement device and the blower or the compressor constitute a particle counter.

10. The continuous atmospheric horizontal dustfall flux measurement apparatus according to claim 2, further comprising:
an aerovane that measures an average wind speed of external air per unit time;
a calculation device that receives the average wind speed value measured by the aerovane and a momentary dustfall amount measurement value measured by the continuous dust amount measurement device as an input value and calculates a momentary external air dustfall concentration on the basis of Equation (2) below:

(momentary external air dustfall concentration)=(momentary dustfall amount measurement value)/((average wind speed measurement value)×(effective opening area of external air inlet))　　(2); and an output device that stores or displays the momentary external air dustfall concentration calculated by the calculation device.

11. The continuous atmospheric horizontal dustfall flux measurement apparatus according to claim 2, wherein a length of each of the partition plates along an axial direction of the side wall is twice or more of a length of the external air inlet along the axial direction of the side wall.

12. The continuous atmospheric horizontal dustfall flux measurement apparatus according to claim 2, wherein a length of each of the partition plates along an axial direction of the side wall is 0.5 times of a length of the dust sampling port along the axial direction.

13. The continuous atmospheric horizontal dustfall flux measurement apparatus according to claim 2, wherein the blower or the compressor suctions a part or all of dustfall flowing into the dust sampling port along with air together with a part of the air inside the dust sampling port, introduces the dustfall and the air into the continuous dust amount measurement device through the suction pipe from the suction port, and discharges the suctioned air from the exhaust port.

14. A continuous atmospheric horizontal dustfall flux measurement method using the continuous atmospheric horizontal dustfall flux measurement apparatus according to claim 2, wherein a value obtained by dividing the amount of the dustfall trapped per unit time by the effective opening area of the external air inlet is calculated as the horizontal flux of the dustfall.

* * * * *